United States Patent
Craighead et al.

(10) Patent No.: US 12,338,487 B2
(45) Date of Patent: Jun. 24, 2025

(54) MULTIOMIC ANALYSIS OF CELL ANALYTES USING MICROFLUIDIC SYSTEMS

(71) Applicant: CORNELL UNIVERSITY, Ithaca, NY (US)

(72) Inventors: Harold G. Craighead, Ithaca, NY (US); Harvey C. Tian, Ithaca, NY (US); David M. Lin, Ithaca, NY (US); Adam J. Bisogni, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 976 days.

(21) Appl. No.: 17/298,533

(22) PCT Filed: Nov. 29, 2019

(86) PCT No.: PCT/US2019/063866
§ 371 (c)(1),
(2) Date: May 28, 2021

(87) PCT Pub. No.: WO2020/113173
PCT Pub. Date: Jun. 4, 2020

(65) Prior Publication Data
US 2022/0010360 A1    Jan. 13, 2022

Related U.S. Application Data

(60) Provisional application No. 62/772,621, filed on Nov. 28, 2018.

(51) Int. Cl.
*C12Q 1/00* (2006.01)
*B01L 3/00* (2006.01)
(Continued)

(52) U.S. Cl.
CPC .......... *C12Q 1/6806* (2013.01); *B01L 3/5027* (2013.01); *B01L 3/502761* (2013.01);
(Continued)

(58) Field of Classification Search
None
See application file for complete search history.

(56) References Cited

U.S. PATENT DOCUMENTS

| | | | |
|---|---|---|---|
| 5,304,487 A | 4/1994 | Wilding et al. | |
| 6,696,022 B1 | 2/2004 | Chan et al. | |

(Continued)

FOREIGN PATENT DOCUMENTS

| | | | |
|---|---|---|---|
| EP | 2714884 A1 | 4/2014 | |
| WO | 2007050040 A1 | 5/2007 | |

(Continued)

OTHER PUBLICATIONS

Zhang et al., "Aptamers selected by cell-SELEX for application in cancer studies," Bioanalysis, 2(5):907-918 (2010).
(Continued)

*Primary Examiner* — Jyoti Nagpaul
(74) *Attorney, Agent, or Firm* — FisherBroyles, LLP; Andrew K. Gonsalves

(57) ABSTRACT

A method for isolating one or more distinct analyte component from a cell sample is disclosed, as well as processes for testing and analyzing the distinct analyte components. The distinct analyte components include: (i) a total protein fraction; (ii) a plasma membrane protein fraction; (iii) a total RNA fraction; (iv) a cytosolic RNA fraction; (v) a cytosolic protein fraction; (vi) a nuclear RNA fraction; (vii) a nuclear protein fraction; (viii) a chromatin fraction comprising genomic DNA (gDNA); (ix) a gDNA markers fraction. This method involves the use of microfluidic device having a cell capture component and a nucleic acid entanglement com-
(Continued)

ponent, where the cell capture component includes a cell capture array having a plurality of cell capture micropillars, where the nucleic acid entanglement component includes a nucleic acid entanglement array having a plurality of nucleic acid entanglement micropillars, and where the microfluidic device operates under continuous flow conditions.

23 Claims, 10 Drawing Sheets

(51) Int. Cl.
  *C12N 15/10*    (2006.01)
  *C12Q 1/6806*    (2018.01)
  *C12M 3/06*    (2006.01)

(52) U.S. Cl.
  CPC .. *C12N 15/1006* (2013.01); *B01L 2200/0668* (2013.01); *B01L 2300/0816* (2013.01); *B01L 2400/086* (2013.01); *C12M 23/16* (2013.01)

(56) References Cited

U.S. PATENT DOCUMENTS

| | | |
|---|---|---|
| 6,977,148 B2 | 12/2005 | Dean et al. |
| 7,384,561 B2 | 6/2008 | Utsunomiya |
| 7,964,978 B1 | 6/2011 | Lee et al. |
| 8,562,918 B2 | 10/2013 | Jovanovich et al. |
| 8,871,446 B2 | 10/2014 | Hong et al. |
| 9,086,406 B2 | 7/2015 | Lee et al. |
| 9,128,091 B2 | 9/2015 | Toner et al. |
| 9,250,242 B2 | 2/2016 | Martin et al. |
| 9,506,845 B2 | 11/2016 | Fowler et al. |
| 9,803,192 B2 | 10/2017 | Craighead et al. |
| 9,926,552 B2 | 3/2018 | Craighead et al. |
| 2002/0081744 A1 | 6/2002 | Chan et al. |
| 2002/0125192 A1 | 9/2002 | Lopez et al. |
| 2003/0143599 A1 | 7/2003 | Makarov et al. |
| 2003/0162181 A1 | 8/2003 | Yang et al. |
| 2004/0050700 A1 | 3/2004 | Lopez-Canovas et al. |
| 2004/0053403 A1 | 3/2004 | Jedrzejewski et al. |
| 2004/0142491 A1 | 7/2004 | Indermuhle et al. |
| 2005/0019819 A1 | 1/2005 | Tooke et al. |
| 2005/0064575 A1 | 3/2005 | Belgrader et al. |
| 2005/0069459 A1 | 3/2005 | Ahn et al. |
| 2006/0133957 A1 | 6/2006 | Knapp et al. |
| 2007/0077547 A1 | 4/2007 | Shvets et al. |
| 2008/0124721 A1 | 5/2008 | Fuchs et al. |
| 2008/0124779 A1 | 5/2008 | Oh et al. |
| 2008/0125330 A1 | 5/2008 | Cady et al. |
| 2008/0160602 A1 | 6/2008 | He et al. |
| 2008/0274905 A1 | 11/2008 | Greene |
| 2009/0098541 A1 | 4/2009 | Southern et al. |
| 2009/0186776 A1 | 7/2009 | Webb et al. |
| 2009/0191563 A1 | 7/2009 | Steemers et al. |
| 2010/0047924 A1 | 2/2010 | Webster et al. |
| 2010/0137163 A1 | 6/2010 | Link et al. |
| 2010/0190146 A1 | 7/2010 | Bynum et al. |
| 2011/0014605 A1 | 1/2011 | Stone |
| 2011/0027873 A1 | 2/2011 | Cho et al. |
| 2011/0212440 A1 | 9/2011 | Viovy et al. |
| 2011/0301058 A1 | 12/2011 | Cheng et al. |
| 2012/0091235 A1 | 4/2012 | Li et al. |
| 2014/0154703 A1 | 6/2014 | Skelley et al. |
| 2014/0193812 A1 | 7/2014 | Hamilton et al. |
| 2014/0194313 A1* | 7/2014 | Craighead .............. C12M 47/10 422/534 |
| 2015/0018226 A1 | 1/2015 | Hansen et al. |
| 2015/0099642 A1 | 4/2015 | Barany et al. |
| 2015/0166987 A1 | 6/2015 | Craighead et al. |
| 2018/0305682 A1 | 10/2018 | Craighead et al. |

FOREIGN PATENT DOCUMENTS

| | | |
|---|---|---|
| WO | 2011017677 A2 | 2/2011 |
| WO | 2011017681 A2 | 2/2011 |
| WO | 2011038241 A1 | 3/2011 |
| WO | 2012162779 A1 | 12/2012 |
| WO | 2014153071 A1 | 9/2014 |
| WO | 2015077441 A2 | 5/2015 |
| WO | 2016154302 A1 | 9/2016 |
| WO | 2017004463 A1 | 1/2017 |
| WO | 2017205267 A1 | 11/2017 |
| WO | 2017205304 A1 | 11/2017 |

OTHER PUBLICATIONS

Dickey et al., "Oligonucleotide aptamers: A next-generation technology for the capture and detection of circulating tumor cells," Methods, 97:94-103 (2016).
Wan et al., "Capture, isolation and release of cancer cells with aptamer-functionalized glass bead array," Lab Chip, 12:4693-4701 (2012).
Phillips et al., "Enrichment of Cancer Cells Using Aptamers Immobilized on a Microfluidic Channel," Anal. Chem., 81:1033-1039 (2009).
Zheng et al., "Aptamer-Functionalized Barcode Particles for the Capture and Detection of Multiple Types of Circulating Tumor Cells," Adv. Mater., 26:7333-7338 (2014).
Xu et al., "Aptamer-Based Microfluidic Device for Enrichment, Sorting, and Detection of Multiple Cancer Cells," Anal. Chem., 81:7436-7442 (2009).
Sheng et al., "Aptamer-Enabled Efficient Isolation of Cancer Cells from Whole Blood Using a Microfluidic Device," Anal. Chem., 84:4199-4206 (2012).
Shen et al., "Specific Capture and Release of Circulating Tumor Cells Using Aptamer-Modified Nanosubstrates," Adv. Mater., 25:2368-2373 (2013).
Chen et al., "Targeted isolation and analysis of single tumor cells with aptamer-encoded microwell array on microfluidic device," Lab Chip, 12:5180-5185 (2012).
Liu et al., "Rare cell chemiluminescence detection based on aptamer-specific capture in microfluidic channels," Biosensors and Bioelectronics, 28:438-442 (2011).
Lin et al., "Assay of multiplex proteins from cell metabolism based on tunable aptamer and microchip electrophoresis," Biosensors and Bioelectronics, 63:105-111 (2015).
Martin et al., "Capturing cancer cells using aptamer-immobilized square capillary channels," Mol. BioSyst., 7:1720-1727 (2011).
Cabodi et al., "Entropic Recoil Separation of Long DNA Molecules," Anal. Chem., 74:5169-5174 (2002).
Benitez et al., "Microfluidic Extraction, Stretching and Analysis of Human Chromosomal DNA from Single Cells," Lab Chip, 12(22):4848-4854 (Nov. 21, 2012).
Saad et al., "Epidermal growth factor receptor T790M mutation-positive metastatic non-small-cell lung cancer: focus on osimertinib (AZD9291)," OncoTargets and Therapy, 10:1757-1766 (2017).
International Searching Authority (USPTO), International Search Report and Written Opinion issued in counterpart PCT/US2019/063866, dated Apr. 8, 2020.

\* cited by examiner

FIG. 9A FIG. 9B

MULTIOMIC ANALYSIS OF CELL ANALYTES USING MICROFLUIDIC SYSTEMS

CROSS-REFERENCE TO RELATED APPLICATIONS

This application is a U.S. National Phase filing under 35 U.S.C. § 371 of International Application No. PCT/US2019/063866, filed Nov. 29, 2019, and published as WO 2020/113173 A1 on Jun. 4, 2020, which claims priority benefit of U.S. Provisional Patent Application Ser. No. 62/772,621, filed Nov. 28, 2018, the disclosures of which are hereby incorporated by reference herein in their entirety.

FIELD OF THE DISCLOSURE

The present disclosure relates to, inter alia, microfluidic and integrated microchannel technologies for use in systems, methods, and processes for multiomic analysis of cell analytes.

BACKGROUND OF THE DISCLOSURE

Analysis of cell analytes is an important area in modern life sciences technologies. While there are a number of single and multi-omic technologies available, there continues to be a need for more efficient, sensitive, and comprehensive methods for studying cell analytes. Such cell analytes include, for example, total protein, plasma membrane protein, nuclear RNA and protein, cytosolic RNA and protein, chromatin, and genomic DNA.

Moreover, there is a need for new and improved technologies so as to aid in studying cancer and various genetic disorders, and particularly for detecting and understanding genetic mutations implicated in various cancers or other genetic disorders.

The present invention is directed to overcoming these and other deficiencies in the art.

SUMMARY

The present disclosure relates to, inter alia, microfluidic and integrated microchannel technologies for use in systems, methods, and processes for multiomic analysis of cell analytes.

In one aspect, the present disclosure provides a method for isolating one or more distinct analyte component from a cell sample, where the one or more distinct analyte component includes: (i) a total protein fraction; (ii) a plasma membrane protein fraction; (iii) a total RNA fraction; (iv) a cytosolic RNA fraction; (v) a cytosolic protein fraction; (vi) a nuclear RNA fraction; (vii) a nuclear protein fraction; (viii) a chromatin fraction comprising genomic DNA (gDNA) regions of open chromatin; (ix) a gDNA markers fraction comprising epigenetic and regulatory markers of gDNA; (x) an amplified gDNA fraction; and/or (xi) a methylated gDNA fraction. This method involves the steps of: (a) providing a microfluidic device having a cell capture component and a nucleic acid entanglement component, where the cell capture component includes a cell capture array having a plurality of cell capture micropillars, where the nucleic acid entanglement component includes a nucleic acid entanglement array having a plurality of nucleic acid entanglement micropillars, and where the microfluidic device operates under continuous flow conditions; (b) capturing one or more cell in the cell capture array of the microfluidic device while being subjected to a continuous flow rate, where the capturing step involves introducing the one or more cell sample into the microfluidic device under sufficient hydrodynamic flow to entrap, by size exclusion, the one or more cell within the cell capture component; (c) treating the one or more captured cell with a sequential workflow procedure under conditions effective to separate one or more distinct analyte component therefrom; and (d) isolating the one or more distinct analyte component in a manner suitable for further testing and/or analysis thereof.

In another aspect, the present disclosure provides to a process for analyzing one or more distinct analyte component from a cell sample. The one or more distinct analyte component is as further described herein. This process involves the steps of: (i) performing the method for isolating one or more distinct analyte component from a cell sample so as to yield the one or more distinct analyte component; and (ii) conducting further testing and/or analysis of the one or more distinct analyte component. Such further testing and/or analysis can include any test or analytical procedure or protocol ordinarily used for any or all of the distinct analyte components described herein.

Various aspects of the present disclosure are also addressed by the following Paragraphs 1-50 and in the noted combinations thereof, as follows:

Paragraph 1: A method for isolating one or more distinct analyte component from a cell sample, said method comprising the steps of: (a) providing a microfluidic device comprising a cell capture component and a nucleic acid entanglement component, wherein said cell capture component comprises a cell capture array comprising a plurality of cell capture micropillars, wherein said nucleic acid entanglement component comprises a nucleic acid entanglement array comprising a plurality of nucleic acid entanglement micropillars, and wherein the microfluidic device operates under continuous flow conditions; (b) capturing one or more cell in the cell capture array of the microfluidic device while being subjected to a continuous flow rate, said capturing step comprising introducing the one or more cell sample into the microfluidic device under sufficient hydrodynamic flow to entrap, by size exclusion, the one or more cell within the cell capture component; (c) treating the one or more captured cell with a sequential workflow procedure under conditions effective to separate one or more distinct analyte component therefrom, wherein said one or more distinct analyte component is selected from the group consisting of: (i) a total protein fraction; (ii) a plasma membrane protein fraction; (iii) a total RNA fraction; (iv) a cytosolic RNA fraction; (v) a cytosolic protein fraction; (vi) a nuclear RNA fraction; (vii) a nuclear protein fraction; (viii) a chromatin fraction comprising genomic DNA (gDNA) regions of open chromatin; (ix) a gDNA markers fraction comprising epigenetic and regulatory markers of gDNA; (x) an amplified gDNA fraction; and (xi) a methylated gDNA fraction; and (d) isolating the one or more distinct analyte component in a manner suitable for further testing and/or analysis thereof.

Paragraph 2: The method according to Paragraph 1, wherein the sequential workflow procedure comprises implementing a separation protocol to separate up to six distinct classes of analyte component from the cell sample, wherein the distinct classes comprise: Class 1: the total protein and plasma membrane protein fractions; Class 2: the total protein, total RNA, cytosolic RNA, and cytosolic protein fractions; Class 3: the total protein, total RNA, nuclear RNA, and nuclear protein fractions; Class 4: the chromatin fraction; Class 5: the gDNA markers and amplified gDNA fractions; and Class 6: the gDNA markers and methylated gDNA fractions, wherein the sequential workflow procedure operates under the following rules: Rule A: only one distinct analyte component can be isolated per class; Rule B: isolation of one or more of the classes may start with any of the classes; Rule C: if more than one class is to be isolated, the order of isolation must proceed progressively along a classification gradient that includes, in sequence, Class 1, Class 2, Class 3, Class 4, Class 5, and Class 6, where Class 1 represents the start of the classification gradient and Class 6 represents the end of the classification gradient; Rule D: if more than one class is to be isolated, the classes to be isolated will begin with an initial class comprising the class closest to the start of the classification gradient and terminate with a terminal class comprising the class closest to the end of the classification gradient; and Rule E: if more than one class is to be isolated, any intermediate class falling between the initial class and the terminal class of the classification gradient may either be omitted or included from the isolating process.

Paragraph 3: The method according to Paragraph 2, wherein the separation protocol is for separating the total protein fraction from the cell sample and comprises the step of: flowing a total protein treatment solution through the microfluidic device under continuous flow conditions effective to release the total protein fraction from the one or more captured cell, thereby causing the total protein fraction to flow out of the microfluidic device.

Paragraph 4: The method according to Paragraph 3, wherein the total protein treatment solution comprises a detergent, a salt, and a chelating agent.

Paragraph 5: The method according to Paragraph 4, wherein the total protein treatment solution comprises a buffer containing Tris (10-50 mM, pH 7-8), NaCl (10-500 mM), and/or KCl (10-500 mM), MgCl2 (0-5 mM), CaCl2 (0-5 mM), detergent (NP40 (0-1%), sodium deoxycholate (0-1%), or SDS (0-1%)), and EDTA (1 uM-10 mM).

Paragraph 6: The method according to Paragraph 2, wherein the separation protocol is for separating the plasma membrane protein fraction from the cell sample and comprises the step of: flowing a plasma membrane protein treatment solution through the microfluidic device under continuous flow conditions effective to cleave proteins from plasma membranes of the one or more captured cell without lysing the plasma membranes, thereby causing the plasma membrane protein fraction to flow out of the microfluidic device.

Paragraph 7: The method according to Paragraph 6, wherein the plasma membrane protein treatment solution comprises a protease a salt, and a chelating agent.

Paragraph 8: The method according to Paragraph 6, wherein the plasma membrane protein treatment solution comprises trypsin (0.01-0.5%) in phosphate buffered saline, with or without EDTA (10 uM-2 mM), at pH 7-8.

Paragraph 9: The method according to Paragraph 6, wherein the flowing of the plasma membrane protein treatment solution is for a period of time under flow ranging from 1-30 minutes.

Paragraph 10: The method according to Paragraph 6, wherein the stable incubation temperature ranges from 20-40 degrees Celsius.

Paragraph 11: The method according to Paragraph 6, wherein the plasma membrane protein treatment solution comprises trypsin (0.01-0.5%) with or without EDTA (10 uM-2 mM), at pH 7-8, under flow ranging from 1-30 minutes, wherein the stable incubation temperature ranges from 20-40 degrees Celsius.

Paragraph 12: The method according to Paragraph 2, wherein the separation protocol is for separating the total RNA fraction from the cell sample and comprises the step of: flowing a total RNA treatment solution through the microfluidic device under continuous flow conditions effective to release the total RNA fraction from the one or more captured cell, thereby causing the total RNA fraction to flow out of the microfluidic device.

Paragraph 13: The method according to Paragraph 12, wherein the total RNA treatment solution comprises a salt, a detergent, and an RNase inhibitor.

Paragraph 14: The method according to Paragraph 12, wherein the total RNA treatment solution comprises a buffer containing Tris (pH 7-8, 1-50 mM), NaCl (25-500 mM), KCl (25-500 mM), detergent (e.g. Triton X-100, 0.25-2%), and RNase inhibitor.

Paragraph 15: The method according to Paragraph 2, wherein the separation protocol is for separating the cytosolic RNA fraction from the cell sample and comprises the step of: flowing a cytosolic RNA treatment solution through the microfluidic device under continuous flow conditions effective to release the cytosolic RNA fraction from the one or more captured cell, thereby causing the cytosolic RNA fraction to flow out of the microfluidic device.

Paragraph 16: The method according to Paragraph 15, wherein the cytosolic RNA treatment solution comprises a detergent, a salt, an RNase inhibitor.

Paragraph 17: The method according to Paragraph 15, wherein the cytosolic RNA treatment solution comprises a buffer containing Tris (pH 7-8, 1-25 mM), NaCl (10-300 mM) and/or KCl (10-300 mM), detergent (e.g. Triton X-100, Tween 20, or NP40, or digitonin 0.1-2%), with RNase inhibitors.

Paragraph 18: The method according to Paragraph 2, wherein the separation protocol is for separating the cytosolic protein fraction from the cell sample and comprises the step of: flowing a cytosolic protein treatment solution through the microfluidic device under continuous flow conditions effective to release the cytosolic protein fraction from the one or more captured cell, thereby causing the cytosolic protein fraction to flow out of the microfluidic device.

Paragraph 19: The method according to Paragraph 18, wherein the cytosolic protein treatment solution comprises a detergent, a salt, and a protease inhibitor.

Paragraph 20: The method according to Paragraph 18, wherein the cytosolic protein treatment solution comprises a buffer containing Tris (pH 7-8, 1-50 mM), NaCl (10-250 mM) and/or KCl (10-250 mM), detergent (e.g. Triton X-100, Tween 20, NP40, or digitonin 0.1-2%), with protease inhibitors.

Paragraph 21: The method according to Paragraph 2, wherein the separation protocol is for separating the nuclear RNA fraction from the cell sample and comprises the step of: flowing a nuclear RNA treatment solution through the microfluidic device under continuous flow conditions effective to release the nuclear RNA fraction from the one or more captured cell, thereby causing the nuclear RNA fraction to flow out of the microfluidic device.

Paragraph 22: The method according to Paragraph 21, wherein the nuclear RNA treatment solution comprises a detergent, a salt, and an RNase inhibitor.

Paragraph 23: The method according to Paragraph 21, wherein the nuclear RNA treatment solution comprises a buffer containing Tris (pH 7-8, 1-50 mM), NaCl (100-500 mM), and/or KCl (100-500 mM), detergent (e.g. Triton X-100, 0.25-2%), and RNase inhibitor.

Paragraph 24: The method according to Paragraph 2, wherein the separation protocol is for separating the nuclear protein fraction from the cell sample and comprises the step of: flowing a nuclear protein treatment solution through the microfluidic device under continuous flow conditions effective to release the nuclear protein fraction from the one or more captured cell, thereby causing the nuclear protein fraction to flow out of the microfluidic device.

Paragraph 25: The method according to Paragraph 24, wherein the nuclear protein treatment solution comprises a detergent, a salt, a protease inhibitor, and a chelating agent.

Paragraph 26: The method according to Paragraph 24, wherein the nuclear protein treatment solution comprises a buffer containing Tris (pH 7-8, 1-50 mM), NaCl (25-500 mM), KCl (25-500 mM), MgCl2 (0-5 mM), CaCl2 (0-5 mM), EDTA (0-2 mM), detergent (e.g. (NP40 (0-1%), sodium deoxycholate (0-1%)), or SDS (0-1%), and protease inhibitors.

Paragraph 27: The method according to Paragraph 2, wherein the separation protocol is for separating the chromatin fraction from the cell sample and comprises the step of: flowing a chromatin treatment solution through the microfluidic device under continuous flow conditions effective to release the chromatin fraction from the one or more captured cell, thereby causing the chromatin fraction to flow out of the microfluidic device.

Paragraph 28: The method according to Paragraph 27, wherein the chromatin treatment solution comprises salts, urea, a detergent, a chelating agent, DTT, RNase inhibitor, and a protease inhibitor.

Paragraph 29: The method according to Paragraph 28, wherein the flowing of the chromatin treatment solution is conducted under gentle heating for a period of time under flow sufficient to allow for activation of native Polymerase II at open chromatin sites to generate nascent RNA transcripts.

Paragraph 30: The method according to Paragraph 29, wherein the gentle heating is at a temperature ranging from 25-39 degrees Celsius and for a period of time ranging from 1-20 minutes.

Paragraph 31: The method according to Paragraph 2, wherein the separation protocol is for separating the gDNA markers fraction from the cell sample and comprises the step of: flowing a gDNA markers treatment solution through the microfluidic device under continuous flow conditions effective to release the gDNA markers fraction from the one or more captured cell, thereby causing the gDNA markers fraction to flow out of the microfluidic device.

Paragraph 32: The method according to Paragraph 31, wherein the gDNA markers treatment solution comprises an enzyme and/or an antibody.

Paragraph 33: The method according to Paragraph 32, wherein the gDNA markers treatment solution comprises a buffer that is intended to integrate Tn5 transposase into regions of open chromatin, or a buffer that is intended to bind to RNA Pol-II that is bound to DNA, or a buffer that is intended to digest regions sensitive to DNAseI, or a buffer that is intended to bind to specific proteins such as transcription factors that are bound to DNA, or a buffer that is intended to digest interlinking regions of nucleosomes, or a buffer that contains antibodies intended to bind to histones containing specification modifications such as lactylation.

Paragraph 34: The method according to Paragraph 2, wherein the separation protocol is for separating the amplified gDNA fraction from the cell sample and comprises the step of: flowing an amplified gDNA treatment solution through the microfluidic device under continuous flow conditions effective to release the amplified gDNA fraction from the one or more captured cell, thereby causing the amplified gDNA fraction to flow out of the microfluidic device.

Paragraph 35: The method according to Paragraph 34, wherein the amplified gDNA treatment solution comprises a denaturant buffer, a neutralization buffer, a polymerase buffer, polymerase (such as Phi29), nucleotides, and primers.

Paragraph 36: The method according to Paragraph 32, wherein the amplified gDNA treatment solution comprises solutions used with an isothermal amplification process such as Qiagen REPLI-g single cell kit (150343) or Qiagen REPLI-g UltraFast Mini kit (150033).

Paragraph 37: The method according to Paragraph 2, wherein the separation protocol is for separating the methylated gDNA fraction from the cell sample and comprises the step of: flowing an methylated gDNA treatment solution through the microfluidic device under continuous flow conditions effective to release the methylated gDNA fraction from the one or more captured cell, thereby causing the methylated gDNA fraction to flow out of the microfluidic device.

Paragraph 38: The method according to Paragraph 37, wherein the methylated gDNA treatment solution comprises a restriction enzyme digest buffer (salts), restriction enzyme, oligonucleotides, and sodium bisulfite.

Paragraph 39: The method according to Paragraph 38, wherein the methylated gDNA treatment solution comprises a restriction enzyme (1-500 U), a restriction enzyme buffer, and a sodium bisulfite conversion reagent.

Paragraph 40: The method according to Paragraph 1, wherein said gDNA is single-stranded gDNA, double-stranded gDNA, or a combination of single- and -double-stranded gDNA.

Paragraph 41: The method according to Paragraph 1, wherein the cell sample is a single cell or multiple cells.

Paragraph 42: The method according to Paragraph 1, wherein the cell sample is selected from the group consisting of a cancer cell, a primary cell type isolated from tissue of a human, an animal, or a plant, and an immortalized cell line.

Paragraph 43: The method according to Paragraph 1, wherein the flow rate ranges from between 0.001 nL/minute and 100 uL/minute.

Paragraph 44: The method according to Paragraph 2, wherein said treating step comprises implementing a combination of the separation protocols to isolate one or more of the distinct analyte components for purposes of single or multiomic analysis thereof.

Paragraph 45: The method according to any one of Paragraphs 2-44, wherein the one or more distinct analyte component comprises a collection of analytes selected from the group consisting of: (a) the plasma membrane protein, cytosolic RNA, nuclear RNA, chromatin, amplified gDNA, and methylated gDNA fractions isolated in sequential order; (b) the plasma membrane protein, cytosolic RNA, nuclear RNA, chromatin, amplified gDNA, and gDNA markers of gDNA fractions isolated in sequential order; (c) the plasma membrane protein, cytosolic protein, nuclear protein, chromatin, amplified gDNA, and methylated gDNA fractions isolated in sequential order; (d) the plasma membrane protein, cytosolic protein, nuclear protein, chromatin, and gDNA markers fractions isolated in sequential order; (e) the plasma membrane protein, cytosolic protein, nuclear RNA, chromatin, amplified gDNA, and methylated gDNA fractions isolated in sequential order; (f) the plasma membrane protein, cytosolic protein, nuclear RNA, chromatin, and gDNA markers fractions isolated in sequential order; (g) the plasma membrane protein, cytosolic RNA, nuclear protein, chromatin, amplified gDNA, and methylated gDNA fractions isolated in sequential order; (h) the plasma membrane protein, cytosolic RNA, nuclear protein, chromatin, and gDNA markers fractions isolated in sequential order; (i) the plasma membrane protein, total RNA, chromatin, amplified gDNA, and methylated gDNA fractions isolated in sequential order; (j) the plasma membrane protein, total RNA, chromatin, and gDNA markers fractions isolated in sequential order; (k) the total protein, chromatin, amplified gDNA, and methylated gDNA fractions isolated in sequential order; (l) the total protein, chromatin, and gDNA markers fractions isolated in sequential order; (m) the total RNA, chromatin, amplified gDNA, and methylated gDNA fractions isolated in sequential order; and (n) the total RNA, chromatin, and gDNA markers fractions isolated in sequential order.

Paragraph 46: A process for analyzing one or more distinct analyte component from a cell sample, said process comprising the steps of: performing the method according to any one of Paragraphs 1-44 to yield one or more distinct analyte component from a cell sample; and conducting further testing and/or analysis of the one or more distinct analyte component.

Paragraph 47: The process according to Paragraph 46, wherein the one or more distinct analyte component is a plasma membrane protein fraction, a total protein fraction, a cytosolic protein fraction, and/or a nuclear protein fraction that is subjected to further testing and/or analysis selected from the group consisting of mass spectrometry, immuno-based detection assays, and aptamer-based detection assays.

Paragraph 48: The process according to Paragraph 46, wherein the one or more distinct analyte component is a total RNA fraction, a cytosolic RNA fraction, a nuclear RNA fraction, and/or a chromatin fraction that is subjected to further testing and/or analysis selected from the group consisting of transcriptome analysis via RNA-seq, targeted gene expression profiling via RT-PCR, RT-qPCR, or NanoString, and qualitative and quantitative characterization such as fragment analyzer, Qubit, or NanoDrop.

Paragraph 49: The process according to Paragraph 46, wherein the one or more distinct analyte component is a gDNA markers fraction and/or an amplified gDNA fraction that is subjected to further testing and/or analysis selected from the group consisting of whole genome sequencing, exome sequencing, targeted re-sequencing, PCR, and qPCR.

Paragraph 50: The process according to Paragraph 46, wherein the one or more distinct analyte component is a methylated gDNA fraction that is subjected to further testing and/or analysis selected from the group consisting of bisulfite conversion analysis, methylation specific PCR, methylation specific qPCR, reduced representation bisulfite sequencing, and whole genome bisulfite sequencing.

These and other objects, features, and advantages of this invention will become apparent from the following detailed description of the various aspects of the invention taken in conjunction with the accompanying drawings.

BRIEF DESCRIPTION OF THE DRAWINGS

FIGS. 9A-9C are micrographs and graphs illustrating data showing that gDNA trapped on micropillars can be recovered using restriction enzymes with high efficiency according to embodiments of the present disclosure. FIG. 9A is a micrograph showing gDNA from lysed cells (multi-cell sample) that was trapped and visualized with PicoGreen. FIG. 9B is a micrograph show that PicoGreen signal disappears post restriction enzyme treatment. FIG. 9C is a graph indicating that ~100% of expected gDNA that was trapped is recovered from the output port post digestion (calculated from # of cells that were trapped in array before lysis).

FIG. 10A is a graph showing data of HeLa gDNA purified through standard kits and digested with a restriction enzyme in a tube (using standard methods). FIG. 10B is a graph showing data of gDNA from ~100 cells that was isolated on micropillars and recovered via restriction digest (same enzyme as in FIG. 10A) according to an embodiment of the present disclosure.

DETAILED DESCRIPTION

Figure 1:
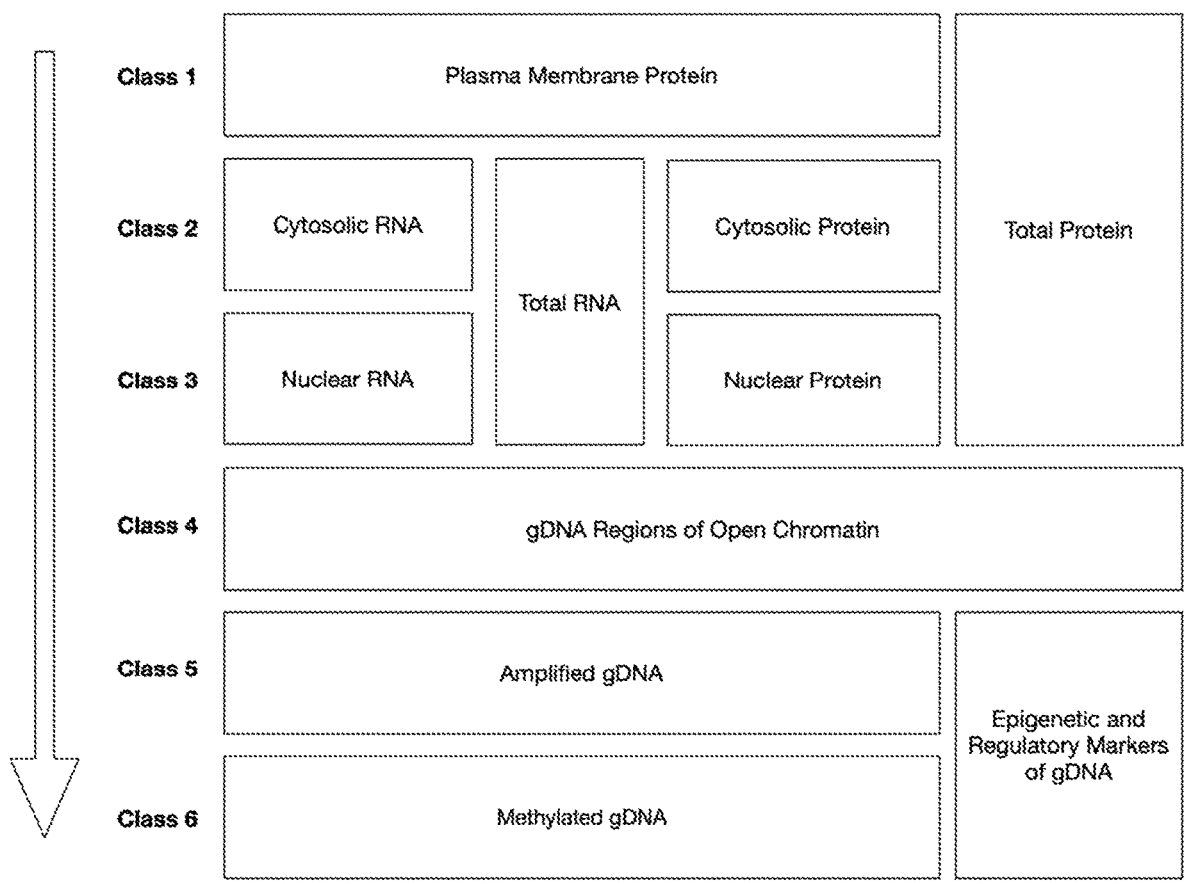
FIG. 1 is a schematic illustrating the six classes (i.e., Classes 1-6) of distinct analyte components of the present disclosure, and in which class or classes each analyte component is grouped. The downward arrow indicates the order of separation of each class of analyte in accordance with a multi-omic separation workflow.
Figure 2:
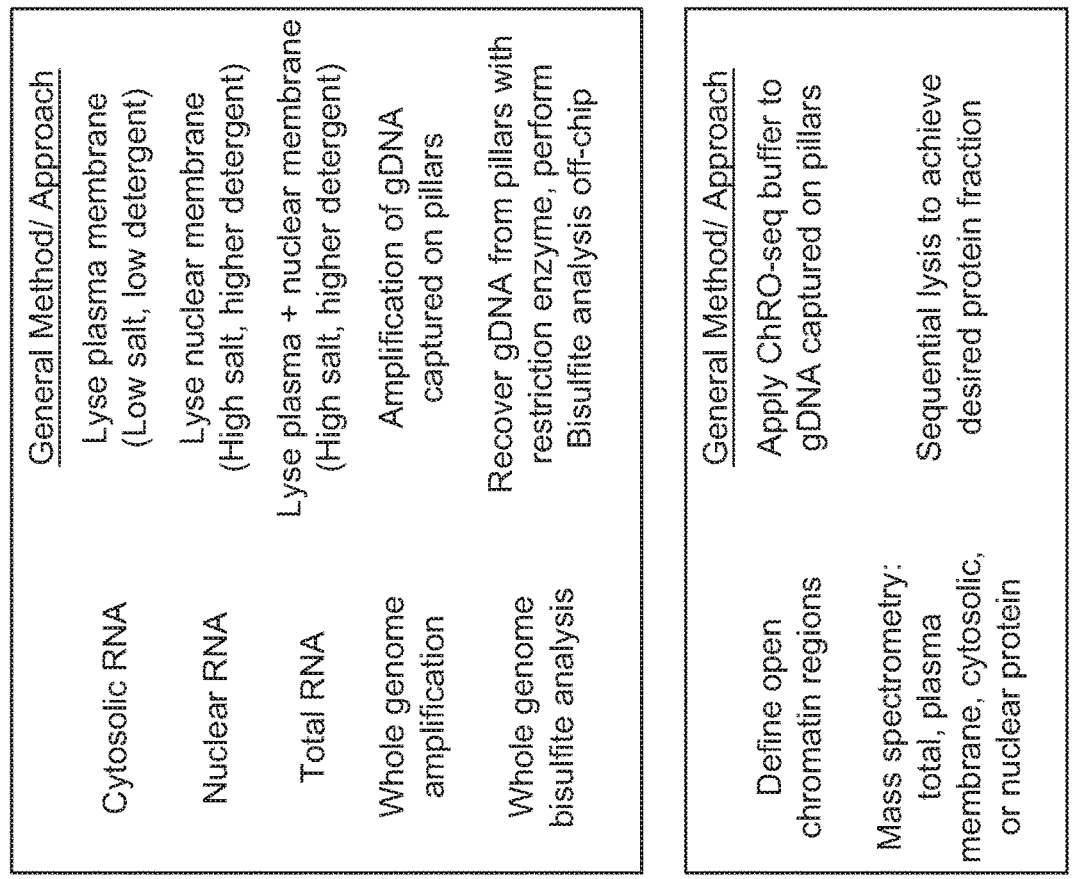
FIG. 2 is a schematic of a graphical summary of some features of certain embodiments of the separation methods and analytical processes of the present disclosure. These separation methods and analytical processes can be used as part of single- and multi-omic workflows using the micropillar technology of the present disclosure.
Figure 2:
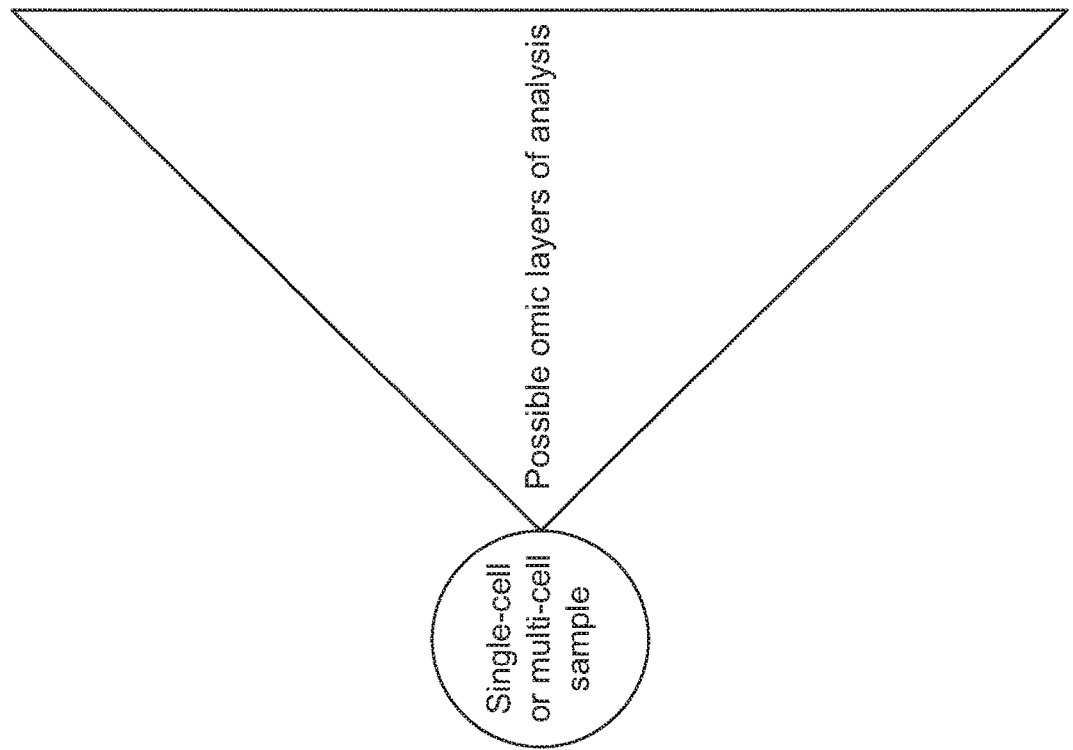

The present disclosure relates to, inter alia, microfluidic and integrated microchannel technologies for use in systems, methods, and processes for multiomic analysis of cell analytes. In certain aspects, the present disclosure relates to, inter alia, microfluidic and integrated microchannel technologies for use in systems and methods for on-chip analysis of nucleic acids and in cell processing systems while under flow conditions.

Method for Isolating Distinct Analyte Components from Cells

In one aspect, the present disclosure relates to a method for isolating one or more distinct analyte component from a cell sample. As used herein, the terms "method for separation," "separation method," "method for isolating," "isolation method," and the like may be used to identify an embodiment of the method for isolating one or more distinct analyte component from a cell sample.

As used herein, a "cell sample" can include a single cell or multiple cells from any source. In certain embodiments, the cell sample can be from, without limitation, a cancer cell, a primary cell type isolated from any tissue of a human, an animal, or a plant, and an immortalized cell line.

As used herein, the term "distinct analyte component" refers to one of eleven different analytes that are separated from a cell sample. Specifically, the eleven distinct analyte components include the following: (i) total protein, which is also referred to herein as a total protein fraction; (ii) plasma membrane protein, which is also referred to herein as a plasma membrane protein fraction; (iii) total RNA, which is also referred to herein as a total RNA fraction; (iv) cytosolic RNA, which is also referred to herein as a cytosolic RNA fraction; (v) cytosolic protein, which is also referred to herein as a cytosolic protein fraction; (vi) nuclear RNA, which is also referred to herein as a nuclear RNA fraction; (vii) nuclear protein, which is also referred to herein as a nuclear protein fraction; (viii) chromatin, which is also referred to herein as a chromatin fraction, and which includes genomic DNA (gDNA) regions of open chromatin; (ix) gDNA markers, which is also referred to herein as a gDNA markers fraction, and which includes epigenetic and regulatory markers of gDNA; (x) amplified gDNA, which is also referred to herein as an amplified gDNA fraction; and (xi) methylated gDNA, which is also referred to herein as a methylated gDNA fraction.

Each of the eleven distinct analyte components are further defined below.

As used herein, the term "total protein fraction" refers to all protein fractions within the cell or cells, including those found in the plasma membrane, cytosolic, and nuclear portions of the cell or cells.

As used herein, the term "plasma membrane protein fraction" refers to only protein residing on and/or within the plasma membrane, which excludes any protein residing in the cytosolic and nuclear portions of the cell or cells.

As used herein, the term "total RNA fraction" refers to all species of RNA within the cell/or cells, including those found in the cytosolic and nuclear portions of the cell or cells.

As used herein, the term "cytosolic RNA fraction" refers to all species of RNA within the cytosolic fraction of the cell or cells, but excludes all RNA residing in the nuclear portion of the cell or cells.

As used herein, the term "cytosolic protein fraction" refers to all proteins within the cytosolic portion of the cell or cells, but excludes all proteins residing in the nuclear portion of the cell or cells.

As used herein, the term "nuclear RNA fraction" refers to all RNA species residing within the nuclear portion of the cell or cells, and excludes all RNA residing in the cytosolic portion of the cell or cells.

As used herein, the term "nuclear protein fraction" refers to all proteins within the nuclear portion of the cell or cells, but excludes all proteins residing in the cytosolic portion of the cell or cells.

As used herein, the term "chromatin fraction" (also referred to herein as the "chromatin fraction comprising genomic DNA (gDNA) regions of open chromatin") refers to all regions of the genome consisting of euchromatin and/or is accessible to RNA polymerase II and excludes regions of the genome that consist of heterochromatin and/or are inaccessible to RNA polymerase II.

As used herein, the term "gDNA markers fraction" (also referred to herein as the "gDNA markers fraction comprising epigenetic and regulatory markers of gDNA") refers to regions of the genome that can be profiled due to their differential sensitivity and response to various treatments such as accessibility via transposase integration, sensitivity to DNAseI, sensitivity to micrococcal nuclease, antibody recognition to RNA Pol-II, transcription factors, or other distinguishing features of chromatin including but not limited to H3K27me3, H3K36me3, H3K9me2/3, H4K20me3, and H3K56Ac.

As used herein, the term "amplified gDNA fraction" refers to single-stranded and double-stranded DNA copies of the gDNA from the cell or cells generated through a genome amplification method such as Multiple Displacement Amplification (MDA) or the like.

As used herein, the term "methylated gDNA fraction" refers to gDNA from the cell or cells, which contains CpG patterns due to 5-methylcytosines.

In accordance with the present disclosure, the method for isolating one or more distinct analyte component from a cell sample involves the steps of: (a) providing a microfluidic device having a cell capture component and a nucleic acid entanglement component, where the cell capture component includes a cell capture array having a plurality of cell capture micropillars, where the nucleic acid entanglement component includes a nucleic acid entanglement array having a plurality of nucleic acid entanglement micropillars, and where the microfluidic device operates under continuous flow conditions; (b) capturing one or more cell in the cell capture array of the microfluidic device while being subjected to a continuous flow rate, where the capturing step involves introducing the one or more cell sample into the microfluidic device under sufficient hydrodynamic flow to entrap, by size exclusion, the one or more cell within the cell capture component; (c) treating the one or more captured cell with a sequential workflow procedure under conditions effective to separate one or more distinct analyte component therefrom; and (d) isolating the one or more distinct analyte component in a manner suitable for further testing and/or analysis thereof.

Suitable flow rates for use in this method can include, without limitation, a flow rate ranging from between 0.001 nL/minute and 100 uL/minute.

In certain embodiments, the treating step involves implementing a combination of the separation protocols to isolate one or more of the distinct analyte components for purposes of single or multiomic analysis thereof.

In one embodiment, the sequential workflow procedure involves implementing a separation protocol to separate up to six distinct classes of analyte component from the cell sample.

As used herein, the six distinct classes of analyte components include the following:

Class 1: the total protein and plasma membrane protein fractions;
Class 2: the total protein, total RNA, cytosolic RNA, and cytosolic protein fractions;
Class 3: the total protein, total RNA, nuclear RNA, and nuclear protein fractions;
Class 4: the chromatin fraction;
Class 5: the gDNA markers and amplified gDNA fractions; and
Class 6: the gDNA markers and methylated gDNA fractions.

These classes are further illustrated in FIG. 1. As shown in FIG. 1, and as stated above, the total protein, total RNA, and gDNA markers fractions span more than one class. Specifically, the total protein fraction is included in Classes 1, 2, and 3, the total RNA fraction is included in Classes 2 and 3, and the gDNA markers fraction is included in Classes 5 and 6. As discussed in more detail herein, the sequential workflow procedure operates under a set of rules in order to take into account the inclusion of the total protein, total RNA, and gDNA markers fractions spanning more than one class.

Regarding the Class 2 and Class 3 analytes, total RNA and total protein have been classified as belonging to both Class 2 and Class 3 (spanning class 2 and class 3), as they encompass both cytosolic and nuclear material. Also, within Classes 2 and 3, in certain embodiments of the present disclosure, RNA cannot be separated from protein on the microfluidic device. For example, if one chooses to separate and collect cytosolic protein and then nuclear protein, those samples will also contain cytosolic RNA and nuclear RNA, respectively. While the micropillars of the microfluidic device of the present disclosure cannot separate protein from RNA, these protein and RNA analytes could in theory be further separated via off-chip methodologies. However, in the context of these protein and RNA analytes, the assumption is that the user will likely be targeting one analyte (RNA or protein) from Class 2 or Class 3.

In accordance with the present disclosure, in one embodiment of the method, the sequential workflow procedure operates under the following rules:

Rule A: only one distinct analyte component can be isolated per class;

Rule B: isolation of one or more of the classes may start with any of the classes;

Rule C: if more than one class is to be isolated, the order of isolation must proceed progressively along a classification gradient that includes, in sequence, Class 1, Class 2, Class 3, Class 4, Class 5, and Class 6, where Class 1 represents the start of the classification gradient and Class 6 represents the end of the classification gradient;

Rule D: if more than one class is to be isolated, the classes to be isolated will begin with an initial class comprising the class closest to the start of the classification gradient and terminate with a terminal class comprising the class closest to the end of the classification gradient; and Rule E: if more than one class is to be isolated, any intermediate class falling between the initial class and the terminal class of the classification gradient may either be omitted or included from the isolating process.

The sequential workflow procedure can be conducted based on the above rules, as well as further guidelines. Suitable guidelines can include, without limitation, those discussed below.

In accordance with the present disclosure, in certain embodiments, the method is suitable for isolating one or more analytes using a separation device such as the microfluidic device described herein.

In one embodiment, the sequential workflow procedure can be guided by the workflow shown in FIG. 1. Informed by the information from FIG. 1, there are certain guidelines that can be followed to practice the methods of isolation and processes of analyzing the analyte components according to the present disclosure.

For example, in one embodiment, the isolation methods and analytical processes of the present disclosure can be conducted using a set of guidelines as follows: (i) up to six different classes of analytes can be recovered; (ii) more than one analyte cannot be isolated within a class (e.g., one cannot isolate nuclear protein and nuclear RNA because they are both in Class 3); (iii) the order of analyte isolation is important, as you cannot go in reverse order (for example, you cannot isolate amplified gDNA (Class 5) and then isolate total RNA (spanning Classes 2-3); and (iv) not all analytes must be recovered in order for the device to be useful (e.g., you can mix and match based on desired outcomes).

As a further example, in another embodiment, the isolation methods and analytical processes of the present disclosure can be conducted using a set of guidelines such as the hierarchy rules for multi-omic workflows of genomic analytes, as follows: (i) a set of basic rules can govern the order and possible combinations by which multiple analytes can be separated and collected using the micropillar technology of the present disclosure; (ii) each level of analysis (analyte, single "omic") is assigned a class (e.g., Class 1-6); (iii) once multiple cells or a single cell is captured, collections of analytes can be initiated at any class, but multi-omic collection of analytes must proceed directionally from Class 1 to Class 6 (see the direction of arrow in FIG. 1); (iv) once a collection is initiated at a given class, analytes from subsequent classes (i.e., higher class number) can be sequentially collected for multi-omic processing; (v) any subsequent class can be skipped if desired (e.g., after collecting an analyte from Class 2, analytes from Classes 4 and 5 could be skipped to just collect analytes from Class 6); (vi) however, analytes from prior classes cannot be retrieved (i.e., one can never go backwards from a given class (e.g., one cannot start at Class 4 and then collect Class 2 analytes); and (vii) analytes from Classes 1-6 can be collected individually, or in any multi-omic combination, so long as the workflow does not violate the preceding rules.

In accordance with the present disclosure, various separation protocols can be used with the microfluidic device to separate the various distinct analyte components from the cell sample. Some suitable separation protocols for each analyte component are provided below.

Total protein separation protocol: In one embodiment, the separation protocol for separating the total protein fraction from the cell sample involves the step of: flowing a total protein treatment solution through the microfluidic device under continuous flow conditions effective to release the total protein fraction from the one or more captured cell, thereby causing the total protein fraction to flow out of the microfluidic device. In one embodiment, the total protein treatment solution can include, without limitation, a detergent, a salt, and a chelating agent. In a particular embodiment, the total protein treatment solution includes a buffer containing Tris (10-50 mM, pH 7-8), NaCl (10-500 mM), and/or KCl (10-500 mM), MgCl2 (0-5 mM), CaCl2 (0-5 mM), detergent (NP40 (0-1%), sodium deoxycholate (0-1%), or SDS (0-1%)), and EDTA (1 uM-10 mM).

Plasma membrane protein separation protocol: In one embodiment, the separation protocol for separating the plasma membrane protein fraction from the cell sample involves the step of: flowing a plasma membrane protein treatment solution through the microfluidic device under continuous flow conditions effective to cleave proteins from plasma membranes of the one or more captured cell without lysing the plasma membranes, thereby causing the plasma membrane protein fraction to flow out of the microfluidic device. In one embodiment, the plasma membrane protein treatment solution can include, without limitation, a protease, a salt, and a chelating agent. In a particular embodiment, the plasma membrane protein treatment solution can include, without limitation, trypsin (0.01-0.5%) in phosphate buffered saline, with or without EDTA (10 uM-2 mM), at pH 7-8. In a particular embodiment, the flowing of the plasma membrane protein treatment solution can be, without limitation, for a period of time under flow ranging from 1-30 minutes. In a particular embodiment, the stable incubation temperature can, without limitation, range from 20-40 degrees Celsius. More particularly, in one embodiment, the plasma membrane protein treatment solution can include, without limitation, trypsin (0.01-0.5%) with or without EDTA (10 uM-2 mM), at pH 7-8, under flow ranging from 1-30 minutes, where the stable incubation temperature ranges from 20-40 degrees Celsius.

Total RNA separation protocol: In one embodiment, the separation protocol for separating the total RNA fraction from the cell sample involves the step of: flowing a total RNA treatment solution through the microfluidic device under continuous flow conditions effective to release the total RNA fraction from the one or more captured cell, thereby causing the total RNA fraction to flow out of the microfluidic device. In one embodiment, the total RNA treatment solution can include, without limitation, a salt, a detergent, and an RNase inhibitor. In a particular embodiment, the total RNA treatment solution can include, without limitation, a buffer containing Tris (pH 7-8, 1-50 mM), NaCl (25-500 mM), KCl (25-500 mM), detergent (e.g. Triton X-100, 0.25-2%), and RNase inhibitor.

Cytosolic RNA separation protocol: In one embodiment, the separation protocol for separating the cytosolic RNA fraction from the cell sample involves the step of: flowing a cytosolic RNA treatment solution through the microfluidic device under continuous flow conditions effective to release the cytosolic RNA fraction from the one or more captured cell, thereby causing the cytosolic RNA fraction to flow out of the microfluidic device. For example, this protocol can be used to lyse the plasma membrane, releasing the cytosolic RNA contents while leaving the nucleus intact, with the cytosolic RNA being collected from an output port of a microfluidic device of the present disclosure. In one embodiment, the cytosolic RNA treatment solution can include, without limitation, a detergent, a salt, an RNase inhibitor. In one embodiment, the cytosolic RNA treatment solution can include, without limitation, a buffer containing Tris (pH 7-8, 1-25 mM), NaCl (10-300 mM) and/or KCl (10-300 mM), detergent (e.g. Triton X-100, Tween 20, or NP40, or digitonin 0.1-2%), with RNase inhibitors.

Cytosolic protein separation protocol: In one embodiment, the separation protocol for separating the cytosolic protein fraction from the cell sample involves the step of: flowing a cytosolic protein treatment solution through the microfluidic device under continuous flow conditions effective to release the cytosolic protein fraction from the one or more captured cell, thereby causing the cytosolic protein fraction to flow out of the microfluidic device. For example, this protocol can be used to lyse plasma membrane but not nuclear membrane, releasing cytosolic protein content to flow out of and be collected from an output port of a microfluidic device of the present disclosure. In one embodiment, the cytosolic protein treatment solution can include, without limitation, a detergent, a salt, and a protease inhibitor. In one embodiment, the cytosolic protein treatment solution can include, without limitation, a buffer containing Tris (pH 7-8, 1-50 mM), NaCl (10-250 mM) and/or KCl (10-250 mM), detergent (e.g. Triton X-100, Tween 20, NP40, or digitonin 0.1-2%), with protease inhibitors.

Nuclear RNA separation protocol: In one embodiment, the separation protocol for separating the nuclear RNA fraction from the cell sample involves the step of: flowing a nuclear RNA treatment solution through the microfluidic device under continuous flow conditions effective to release the nuclear RNA fraction from the one or more captured cell, thereby causing the nuclear RNA fraction to flow out of the microfluidic device. In one embodiment, the nuclear RNA treatment solution can include, without limitation, a detergent, a salt, and an RNase inhibitor. In one embodiment, the nuclear RNA treatment solution can include, without limitation, a buffer containing Tris (pH 7-8, 1-50 mM), NaCl (100-500 mM), and/or KCl (100-500 mM), detergent (e.g. Triton X-100, 0.25-2%), and RNase inhibitor.

Nuclear protein separation protocol: In one embodiment, the separation protocol for separating the nuclear protein fraction from the cell sample involves the step of: flowing a nuclear protein treatment solution through the microfluidic device under continuous flow conditions effective to release the nuclear protein fraction from the one or more captured cell, thereby causing the nuclear protein fraction to flow out of the microfluidic device. In one embodiment, the nuclear protein treatment solution can include, without limitation, a detergent, a salt, a protease inhibitor, and a chelating agent. In one embodiment, the nuclear protein treatment solution can include, without limitation, a buffer containing Tris (pH 7-8, 1-50 mM), NaCl (25-500 mM), KCl (25-500 mM), MgCl2 (0-5 mM), CaCl2 (0-5 mM), EDTA (0-2 mM), detergent (e.g. (NP40 (0-1%), sodium deoxycholate (0-1%)), or SDS (0-1%), and protease inhibitors.

Chromatin separation protocol: In one embodiment, the separation protocol for separating the chromatin fraction from the cell sample involves the step of: flowing a chromatin treatment solution through the microfluidic device under continuous flow conditions effective to release the chromatin fraction from the one or more captured cell, thereby causing the chromatin fraction to flow out of the microfluidic device. In one embodiment, the chromatin treatment solution can include, without limitation, salts, urea, a detergent, a chelating agent, DTT, RNase inhibitor, and a protease inhibitor. In one embodiment, the flowing of the chromatin treatment solution is conducted, without limitation, under gentle heating for a period of time under flow sufficient to allow for activation of native Polymerase II at open chromatin sites to generate nascent RNA transcripts. In one embodiment, the gentle heating is, without limitation, at a temperature ranging from 25-39 degrees Celsius and for a period of time ranging from 1-20 minutes.

gDNA markers separation protocol: In one embodiment, the separation protocol for separating the gDNA markers fraction from the cell sample involves the step of: flowing a gDNA markers treatment solution through the microfluidic device under continuous flow conditions effective to release the gDNA markers fraction from the one or more captured cell, thereby causing the gDNA markers fraction to flow out of the microfluidic device. In one embodiment, the gDNA markers treatment solution can include, without limitation, an enzyme and/or an antibody.

In one embodiment, the gDNA markers treatment solution can include, without limitation, a buffer that is intended to integrate Tn5 transposase into regions of open chromatin (see Buenrostro J D, Wu B, Litzenburger U M, et al. Single-cell chromatin accessibility reveals principles of regulatory variation. *Nature.* 2015523(7561):486-490; Buenrostro S D, Wu B, Chang H Y, Greenleaf W J. ATAC-seq: A Method for Assaying Chromatin Accessibility Genome-Wide. *Curr Protoc Mol Biol.* 2015; 109:21.29.1-

21.29.9. Published 2015 Jan. 5.; Buenrostro, J., Giresi, P., Zaba, L. et al. Transposition of native chromatin for fast and sensitive epigenomic profiling of open chromatin, DNA-binding proteins and nucleosome position. *Nat Methods* 10, 1213-1218 (2013)).

In one embodiment, the gDNA markers treatment solution can include, without limitation, a buffer that is intended to bind to RNA Pol-II that is bound to DNA (see Sun H, Wu J, Wickramasinghe P, et al. Genome-wide mapping of RNA Pol-II promoter usage in mouse tissues by ChIP-seq. *Nucleic Acids Res.* 2011; 39(1):190-201).

In one embodiment, the gDNA markers treatment solution can include, without limitation, a buffer that is intended to digest regions sensitive to DNAseI (see Thurman, R., Rynes, E., Humbert, R. et al. The accessible chromatin landscape of the human genome. *Nature* 489, 75-82 (2012); Song L, Crawford G E. DNase-seq: a high-resolution technique for mapping active gene regulatory elements across the genome from mammalian cells. *Cold Spring Harb Protoc.* 2010; 2010(2).pdb.prot5384).

In one embodiment, the gDNA markers treatment solution can include, without limitation, a buffer that is intended to bind to specific proteins such as transcription factors that are bound to DNA (see Johnson D S, Mortazavi A, Myers R M, Wold B. Science. 2007 Jun. 8; 316(5830):1497-1502).

In one embodiment, the gDNA markers treatment solution can include, without limitation, a buffer that is intended to digest interlinking regions of nucleosomes (see Chereji, R. V., Bryson, T. D. & Henikoff, S. Quantitative MNase-seq accurately maps nucleosome occupancy levels. *Genome Biol* 20, 198 (2019); Ramani V, Qiu R, Shendure J. High Sensitivity Profiling of Chromatin Structure by MNase-SSP. *Cell Rep.* 2019; 26(9):2465-2476.e4).

In one embodiment, the gDNA markers treatment solution can include, without limitation, a buffer that contains antibodies intended to bind to histones containing specification modifications such as lactylation (see Zhang, D., Tang, Z., Huang, H. et al. Metabolic regulation of gene expression by histone lactylation. *Nature* 574, 575-580 (2019)).

Amplified gDNA separation protocol: In one embodiment, the separation protocol for separating the amplified gDNA fraction from the cell sample involves the step of: flowing an amplified gDNA treatment solution through the microfluidic device under continuous flow conditions effective to release the amplified gDNA fraction from the one or more captured cell, thereby causing the amplified gDNA fraction to flow out of the microfluidic device. In one embodiment, the amplified gDNA treatment solution can include, without limitation, a denaturant buffer, a neutralization buffer, a polymerase buffer, polymerase (such as Phi29), nucleotides, and primers. In one embodiment, the amplified gDNA treatment solution can include, without limitation, solutions used with an isothermal amplification process such as Qiagen REPLI-g single cell kit (150343) or Qiagen REPLI-g UltraFast Mini kit (150033).

Methylated gDNA separation protocol: In one embodiment, the separation protocol for separating the methylated gDNA fraction from the cell sample involves the step of: flowing an methylated gDNA treatment solution through the microfluidic device under continuous flow conditions effective to release the methylated gDNA fraction from the one or more captured cell, thereby causing the methylated gDNA fraction to flow out of the microfluidic device. In one embodiment, the methylated gDNA treatment solution can include, without limitation, a restriction enzyme digest buffer (salts), restriction enzyme, oligonucleotides, and sodium bisulfite. In one embodiment, the methylated gDNA treatment solution can include, without limitation, a restriction enzyme (1-500 U), a restriction enzyme buffer, and a sodium bisulfite conversion reagent.

In certain embodiments, the method of the present disclosure for isolating one or more distinct analyte component from a cell can be used to isolate various forms of gDNA. For example, the method can be used to isolate single-stranded gDNA (ssgDNA), double-stranded gDNA (dsgNDA), or a combination of single- and -double-stranded gDNA. Various protocols for isolating the different forms of gDNA can include, without limitation, the following: (i) for dsgDNA, the following methods can be used to remove and recover the gDNA: restriction enzyme digestion (37 C for 30'), sonication, heat (45-95 C), DNAseI, increased flow rate (0.001 nL/min to 100 uL/min) or photocleaving; and (ii) for ssgDNA, the same methods can be applied except if a restriction enzyme digestion is used, a brief annealing step with short oligos complementary to the restrictions site is required to provide a double stranded template for the enzyme to recognize. This can be performed with −5 wobble sites at the 5' and 3' ends of the oligo.

In accordance with the method of the present disclosure, various combinations of distinct analyte components can be separated and isolated from the cell sample. Certain suitable combinations are described below, where the one or more distinct analyte component includes a collection of analytes separated and isolated from the cell sample according to a particular sequence of analyte separation/isolation.

Combination 1: In one embodiment, the distinct analyte components are isolated from the cell sample in the following sequential order: the plasma membrane protein, cytosolic RNA, nuclear RNA, chromatin, amplified gDNA, and methylated gDNA fractions isolated in sequential order.

Combination 2: In one embodiment, the distinct analyte components are isolated from the cell sample in the following sequential order: the plasma membrane protein, cytosolic RNA, nuclear RNA, chromatin, amplified gDNA, and gDNA markers of gDNA fractions isolated in sequential order.

Combination 3: In one embodiment, the distinct analyte components are isolated from the cell sample in the following sequential order: the plasma membrane protein, cytosolic protein, nuclear protein, chromatin, amplified gDNA, and methylated gDNA fractions isolated in sequential order.

Combination 4: In one embodiment, the distinct analyte components are isolated from the cell sample in the following sequential order: the plasma membrane protein, cytosolic protein, nuclear protein, chromatin, and gDNA markers fractions isolated in sequential order.

Combination 5: In one embodiment, the distinct analyte components are isolated from the cell sample in the following sequential order: the plasma membrane protein, cytosolic protein, nuclear RNA, chromatin, amplified gDNA, and methylated gDNA fractions isolated in sequential order.

Combination 6: In one embodiment, the distinct analyte components are isolated from the cell sample in the following sequential order: the plasma membrane protein, cytosolic protein, nuclear RNA, chromatin, and gDNA markers fractions isolated in sequential order.

Combination 7: In one embodiment, the distinct analyte components are isolated from the cell sample in the following sequential order: the plasma membrane protein, cytosolic RNA, nuclear protein, chromatin, amplified gDNA, and methylated gDNA fractions isolated in sequential order.

Combination 8: In one embodiment, the distinct analyte components are isolated from the cell sample in the following sequential order: the plasma membrane protein, cytosolic RNA, nuclear protein, chromatin, and gDNA markers fractions isolated in sequential order.

Combination 9: In one embodiment, the distinct analyte components are isolated from the cell sample in the following sequential order: the plasma membrane protein, total RNA, chromatin, amplified gDNA, and methylated gDNA fractions isolated in sequential order.

Combination 10: In one embodiment, the distinct analyte components are isolated from the cell sample in the following sequential order: the plasma membrane protein, total RNA, chromatin, and gDNA markers fractions isolated in sequential order.

Combination 11: In one embodiment, the distinct analyte components are isolated from the cell sample in the following sequential order: the total protein, chromatin, amplified gDNA, and methylated gDNA fractions isolated in sequential order.

Combination 12: In one embodiment, the distinct analyte components are isolated from the cell sample in the following sequential order: the total protein, chromatin, and gDNA markers fractions isolated in sequential order.

Combination 13: In one embodiment, the distinct analyte components are isolated from the cell sample in the following sequential order: the total RNA, chromatin, amplified gDNA, and methylated gDNA fractions isolated in sequential order.

Combination 14: In one embodiment, the distinct analyte components are isolated from the cell sample in the following sequential order: the total RNA, chromatin, and gDNA markers fractions isolated in sequential order.

Process for Analyzing One or More Distinct Analyte Component from a Cell Sample

In another aspect, the present disclosure relates to a process for analyzing one or more distinct analyte component from a cell sample. The one or more distinct analyte component is as further described herein. This process involves the steps of: (i) performing the method for isolating one or more distinct analyte component from a cell sample, thereby isolating the one or more distinct analyte component from the cell sample; and (ii) conducting further testing and/or analysis of the isolated one or more distinct analyte component. Such further testing and/or analysis can include any test or analytical procedure or protocol suitable for use in testing or analyzing the subject analyte component, the analyte component being one of those as defined herein. As used herein, the terms "process for analysis" and "analytical process" and the like may be used to identify an embodiment of the process for analyzing one or more distinct analyte component from a cell sample.

In certain embodiments of this process, the one or more distinct analyte component is a plasma membrane protein fraction, a total protein fraction, a cytosolic protein fraction, and/or a nuclear protein fraction that is subjected to further testing and/or analysis that involves, without limitation, mass spectrometry, immuno-based detection assays, and aptamer-based detection assays.

In certain embodiments of this process, the one or more distinct analyte component is a total RNA fraction, a cytosolic RNA fraction, a nuclear RNA fraction, and/or a chromatin fraction that is subjected to further testing and/or analysis that involves, without limitation, transcriptome analysis via RNA-seq, targeted gene expression profiling via RT-PCR, RT-qPCR, or NanoString, and qualitative and quantitative characterization such as fragment analyzer, Qubit, or NanoDrop.

In certain embodiments of this process, the one or more distinct analyte component is a gDNA markers fraction and/or an amplified gDNA fraction that is subjected to further testing and/or analysis that involves, without limitation, whole genome sequencing, exome sequencing, targeted re-sequencing, PCR, and qPCR.

In certain embodiments of this process, the one or more distinct analyte component is a methylated gDNA fraction that is subjected to further testing and/or analysis that involves, without limitation, bisulfite conversion analysis, methylation specific PCR, methylation specific qPCR, reduced representation bisulfite sequencing, and whole genome bisulfite sequencing.

Protocols for Separation and Analysis

Various protocols can be used in the separation methods and analytical processes of the present disclosure. As shown herein, there are eleven different and distinct analyte components, with these analytes being organized into six classes of analytes (Classes 1-6) (see FIG. 1). Also as shown herein, there are a number of combinations of how the different analytes can be separated from a cell sample, and in which order (see Combinations 1-14 above). In accordance with the present disclosure, any subset of analytes for any of these combinations could be assayed based on which buffers are used and in what order. Thus, in accordance with the separation methods and analytical processes of the present disclosure, it is possible to obtain a subset of any of the analytes based on which sequence of buffers the user chooses. For reference purposes, suitable buffers/methods for separation and processes of analysis for each of the analytes are disclosed in Table 1, although the methods and processes of the present disclosure are not meant to be limited to just those disclosed in Table 1.

TABLE 1

| | Analyte | Buffer/Method for Separation | Processes of Analysis |
|---|---|---|---|
| 1 | Total Protein | Flow buffer containing Tris (10-50 mM, pH 7-8), NaCl (25-500 mM), and/or KCl (25-500 mM), MgCl2 (0-5 mM), CaCl2 (0-5 mM), detergent (NP40 (0-1%), sodium deoxycholate (0-1%), SDS (0-1%) and EDTA (1 uM-10 mM) and protease inhibitors for several minutes (1-30 minutes) at room temp (22-27 C.) or chilled to 4 C. Total protein can be collected at outport. Flow ranges: 0.001 psi-100 psi | Mass Spectrometry, various methodologies such as immuno or aptamer based detection assays |
| 2 | Plasma membrane | Flow solution of trypsin (0.01-0.5%) with or without EDTA (10 uM-2 mM), | Mass Spectrometry, various methodologies such as immuno |

TABLE 1-continued

| | Analyte | Buffer/Method for Separation | Processes of Analysis |
|---|---|---|---|
| | protein | pH 7-8. Incubate for several minutes under flow (1-30 minutes), maintaining a stable incubation temperature. This will result in cleaving the proteins from the plasma membrane but not lysing the plasma membrane itself. Plasma membrane proteins will therefore flow towards output port for collection while remaining analytes of cell will remain in capture array. Flow ranges: 0.001 psi-100 psi | or aptamer based detection assays |
| 3 | Total RNA | Flow buffer containing Tris (pH 7-8, 1-50 mM), NaCl (25-500 mM), KCl (25-500 mM), detergent (e.g. Triton X-100, 0.25-2%), and RNase inhibitor. Incubate for several minutes (1-30 minutes) at room temp (22-27 C.) or chilled (4-20 C.). Flow ranges: 0.001 psi-100 psi. Total RNA is collected at output port. | Transcriptome analysis via RNA-Seq; targeted profiling via RT-PCR, RT-qPCR, NanoString; qualitative and quantitative characterization such as Fragment Analyzer, Qubit, Nanodrop. |
| 4 | Cytosolic RNA | Flow buffer containing Tris (pH 7-8, 1-25 mM), NaCl (10-300 mM) and/or KCl (10-300 mM), detergent (e.g. Triton X-100, Tween 20, or NP40, or digitonin 0.1-2%), with RNase inhibitors. Incubate for several minutes (1-20 minutes) at room temp (22-27 C.) or chilled (4-20 C.). Flow ranges: 0.001 psi-100 psi. This will lyse the plasma membrane, releasing the cytosolic RNA contents while leaving the nucleus in tact. Cytosolic RNA is collected at the output port. | Transcriptome analysis via RNA-Seq; targeted profiling via RT-PCR, RT-qPCR, NanoString; qualitative and quantitative characterization such as Fragment Analyzer, Qubit, Nanodrop. |
| 5 | Cytosolic Protein | Flow buffer containing Tris (pH 7-8, 1-50 mM), NaCl (10-250 mM) and/or KCl (10-250 mM), detergent (e.g. Triton X-100, Tween 20, NP40, or digitonin 0.1-2%), with protease inhibitors. Incubate for several minutes (1-20 minutes) at room temp (22-27 C.) or chilled (4-20 C.). Flow ranges: 0.001 psi-100 psi. This will lyse plasma membrane but not nuclear membrane, releasing cytosolic protein content to flow to output port. | Mass Spectrometry, various methodologies such as immuno or aptamer based detection assays |
| 6 | Nuclear RNA | Flow buffer containing Tris (pH 7-8, 1-50 mM), NaCl (100-500 mM) and/or KCl (100-500 mM), detergent (e.g. Triton X-100, 0.25-2%), and RNase inhibitor. Incubate for several minutes (1-20 minutes) at room temp (22-27 C.) or chilled (4-20 C.). Flow ranges: 0.001 psi-100 psi. This will release nuclear RNA to the output port, while gDNA released will be captured on the micropillars. | Transcriptome analysis via RNA-Seq; targeted profiling via RT-PCR, RT-qPCR, NanoString; qualitative and quantitative characterization such as Fragment Analyzer, Qubit, Nanodrop. |
| 7 | Nuclear Protein | Flow buffer containing Tris (pH 7-8, 1-50 mM), NaCl (25-500 mM), KCl (25-500 mM), MgCl2 (0-5 mM), CaCl2 (0-5 mM), detergent (e.g. NP40 (0-1%), sodium deoxycholate (0-1%)), SDS (0-1%) and protease inhibitors. Incubate for several minutes (1-20 minutes) at room temp (22-27 C.) or chilled (4-20 C.). Flow ranges: 0.001 psi-100 psi. This will release nuclear protein to the output port, while gDNA released will be captured on the micropillars. | Mass Spectrometry, various methodologies such as immuno or aptamer based detection assays |
| 8 | gDNA Regions of Open Chromatin | A buffer for Chromatin Run On-Seq, cited below, is applied to gDNA which has not been denatured and still retains native chromatin states. Upon gentle heating (22-39 C.), the buffer will allow for the activation native Polymerase II at open chromatin sites to generate nascent RNA transcripts. After a brief incubation period (1-20 minutes), the nascent RNA transcripts are collected from the output port. Flow ranges: 0.001 psi-100 psi. These transcripts are then processed and mapped back to the genome to determine sites of open chromatin. | Transcriptome analysis via RNA-Seq; targeted profiling via RT-PCR, RT-qPCR, NanoString; qualitative and quantitative characterization such as Fragment Analyzer, Qubit, Nanodrop. |

TABLE 1-continued

| Analyte | Buffer/Method for Separation | Processes of Analysis |
|---|---|---|
| | Buffer: modified as needed from (Chu, T., Rice, E. J., Booth, G. T. et al. Chromatin run-on and sequencing maps the transcriptional regulatory landscape of glioblastoma multiforme. Nat Genet 50, 1553-1564 (2018). | |
| 9 Amplified gDNA | Previously described in U.S. Pat. No. 9,926,552 B2. gDNA trapped on pillar as single stranded, double stranded, or a combination of both can be amplified using any isothermal amplification technique (such as Phi29 based Multiple Displacement Amplification). Incubation time can range from 30 minutes to 24 hours at a constant range (25 to 40 C.). While the genome is being amplified, amplicons flow towards the output port. At the end of the incubation, 6M guanidinium thiocyanate is briefly flushed (1-15 minutes) to facilitate release of any remnant amplicons and Phi29 from the gDNA template. Flow ranges: 0.001 psi-100 psi. | Whole genome sequencing, exome sequencing, targeted re-sequencing, PCR, qPCR. |
| 10 Methylated gDNA | gDNA retaining methylation modifications can either be removed for off-chip processing, or processed partially on the chip and then removed. To recover gDNA for off-chip processing: method is dependent on which class preceded it because separations via classes 1-4 (plasma membrane, total protein, cytosolic protein, nuclear protein, total RNA, cytosolic RNA, nuclear RNA) can retain native double stranded-gDNA, whereas class 5 (amplified gDNA) analysis will generate mostly single stranded-gDNA, or a mix of double stranded- and single stranded-gDNA. Our methods are capable of handling gDNA as ss, ds, or combination of both. For dsgDNA, the following methods can be used to remove and recover the gDNA: standard restriction enzyme digestion (30-39 C. for 5-45 minutes), sonication, heat (45-95 C.), DNAseI treatment, increased flow rate (0.001 nL/min to 100 uL/min) or photocleaving. For ssgDNA, the same methods can be applied except if a restriction enzyme digestion method is to be used, a brief annealing step with short oligos complementary to the restrictions site is required to provide a double stranded template for the enzyme to recognize. Annealing can occur using primers (5 uM to 500 nM) with wobble sites (2-5) at the 5' and 3' ends of the oligo. After heating the oligos at 95 C. for 5-10 minutes, they can be applied to the sample under flow and an annealing step program is performed slowly over decreasing temperature to maximize annealing (95 C. to 4 C.). After annealing, digestion can be performed as stated above. To process methylated gDNA on chip: Alternatively, the first steps of methylation analysis can be performed on the device prior to releasing the gDNA from the micropillars. This could include on-chip bisulfite conversion, performed using standard kits (e.g. Zymo Methyl Pico-Seq). Upon treatment with conversion reagent, gDNA will be fragmented and be released from the pillars, which can then be collected at the output port and further processed off chip. | Whole genome bisulfite sequencing, reduced representative bisulfite sequencing (RRBS), methylation specific PCR, methylation specific qPCR, Methylated DNA immunoprecipitation-Seq (MeDIP-Seq) |

TABLE 1-continued

| Analyte | Buffer/Method for Separation | Processes of Analysis |
|---|---|---|
| | Other methylation methods that would be compatible with initial processing on chip includes methylation sensitive digestion approaches such as MeDIP-Seq (Boers R, Boers J, de Hoon B, et al. Genome-wide DNA methylation profiling using the methylation-dependent restriction enzyme LpnPI. *Genome Res.* 2018; 28(1): 88-99) | |
| 11 Epigenetic and Regulatory Markers of gDNA | Several different methods could be employed on chip to assess various markers of epigenetic and regulatory status. These include standard methods in the field that would be adapted to the device by flowing on the specified treatment buffer (adapted method from citations), and then collecting the treated fragments in the output port to prepare for sequencing. The following methods could be applied to gDNA trapped on the micropillars that retains epigenetic modifications and regulatory markers ATAC-Seq<br>Buenrostro J D, Wu B, Litzenburger U M, et al. Single-cell chromatin accessibility reveals principles of regulatory variation. *Nature.* 2015; 523(7561): 486-490.<br>Buenrostro J D, Wu B, Chang H Y, Greenleaf W J. ATAC-seq: A Method for Assaying Chromatin Accessibility Genome-Wide. *Curr Protoc Mol Biol.* 2015, 109: 21.29.1-21.29.9. Published 2015 Jan. 5.<br>Buenrostro, J., Giresi, P., Zaba, L. et al. Transposition of native chromatin for fast and sensitive epigenomic profiling of open chromatin, DNA-binding proteins and nucleosome position. *Nat Methods* 10, 1213-1218 (2013).<br>RNA-Pol-II binding<br>Sun H, Wu J, Wickramasinghe P, et al. Genome-wide mapping of RNA Pol-II promoter usage in mouse tissues by ChIP-seq. *Nucleic Acids Res.* 2011; 39(1): 190-201.<br>Nucleosome occupancy<br>Chereji, R. V., Bryson, T. D. & Henikoff, S. Quantitative MNase-seq accurately maps nucleosome occupancy levels. *Genome Biol* 20, 198 (2019).<br>Ramani V, Qiu R, Shendure J. High Sensitivity Profiling of Chromatin Structure by MNase-SSP. *Cell Rep.* 2019; 26(9): 2465-2476.e4.<br>DNAseI hypersensitivity<br>Thurman, R., Rynes, E., Humbert, R. et al. The accessible chromatin landscape of the human genome. *Nature* 489, 75-82 (2012).<br>Song L, Crawford G E. DNase-seq: a high-resolution technique for mapping active gene regulatory elements across the genome from mammalian cells. *Cold Spring Harb Protoc.* 2010; 2010(2): pdb.prot5384.<br>Lactylation<br>Zhang, D., Tang, Z., Huang, H. et al. Metabolic regulation of gene expression by histone lactylation. *Nature* 574, 575-580 (2019).<br>ChIP-Seq<br>Science. 2007 Jun. 8; 316(5830): 1497-1502 | Various sequencing methods |

Various aspects, components, devices, protocols, systems, and embodiments for use in performing the separation methods and/or analytical processes of the present disclosure are further described in, but not limited to, the following: PCT/US2017/033789 (WO 2017/205267-A1), entitled "Multifunctional Microfluidic Device for Capturing Target Cells and Analyzing Genomic DNA Isolated from the Target Cells While Under Flow Conditions"; PCT/US2017/033885 (WO 2017/205304-A1), entitled "Single Cell Whole Genome Amplification Via Micropillar Arrays Under Flow Conditions"; U.S. Pat. No. 9,803,192 (US2015/0166987-A1), entitled "Programmable and Reconfigurable Microcolumn Affinity Chromatography Device, System, and Methods of Use Thereof"; and U.S. Pat. No. 9,926,552, entitled "Microfluidic Device for Extracting, Isolating, and Analyzing DNA from Cells," the disclosures of which are hereby incorporated herein by reference.

More specifically, PCT/US2017/033789 (WO 2017/205267-A1) and PCT/US2017/033885 (WO 2017/205304-A1), describe various microfluidic devices that can be used for capturing one or more selected cells and separating genomic DNA of these cells from other cellular components for analysis. Therefore, the disclosures contained in PCT/US2017/033789 (WO 2017/205267-A1) and PCT/US2017/033885 (WO 2017/205304-A1) can be used with the devices, systems, and methods of the present disclosure.

The devices described in PCT/US2017/033789 (WO 2017/205267-A1) and PCT/US2017/033885 (WO 2017/205304-A1) utilize microfluidic devices containing microstructures to capture selected cells by size or affinity binding. By lysing the captured cells the genomic DNA can be immobilized in the device and separated from the other components of the lysed cells.

In accordance with the present disclosure, similar devices to those described in PCT/US2017/033789 (WO 2017/205267-A1) and PCT/US2017/033885 (WO 2017/205304-A1) may be used to generate 'multi-omic' information (multiple genomic-type data) from single cells. In certain embodiments, because of the device's structure, after lysis of the captured cell(s), the RNA is washed downstream and can be removed from the outlet port. This can then be amplified to generate transcriptomic data. In accordance with the present disclosure, a lysis buffer can be identified that would not strip histones from the DNA, and allow us to analyze open chromatin status on the captured chromatin bound to the pillars. Then the histones could be removed by flowing in a harsher lysis buffer, and one would be able to amplify the remaining genomic DNA. This concept of multi-omic analysis (RNA, open chromatin, and genomic DNA) on the device is one aspect of the present disclosure.

EXAMPLES

The following examples are intended to illustrate particular embodiments of the present disclosure, but are by no means intended to limit the scope of the present disclosure.

Example 1

Preliminary Studies on Methods for Performing Multi-Omic Analysis of Cells

The present disclosure provides a method for performing multi-omic analysis of cells. During preliminary testing of embodiments of the methods and processes of the present disclosure, various experiments were performed.

In one preliminary study, unexpected results were obtained from initial RNA studies. As a test case, we flowed immortalized HeLa cells into the device and captured ~50-100 cells (using an earlier iteration of the device that does not capture single cells). We lysed the cells and obtained the RNA from the output port. After amplification of the RNA using a commercial kit, the RNA was sequenced. We then mapped the RNA reads back to the reference human genome. For comparison, we used data from the ENCODE consortium, who had previously generated transcriptome data from bulk RNA samples. We also compared it against data from single cell HeLa and 3T3 datasets.

Figure 3:
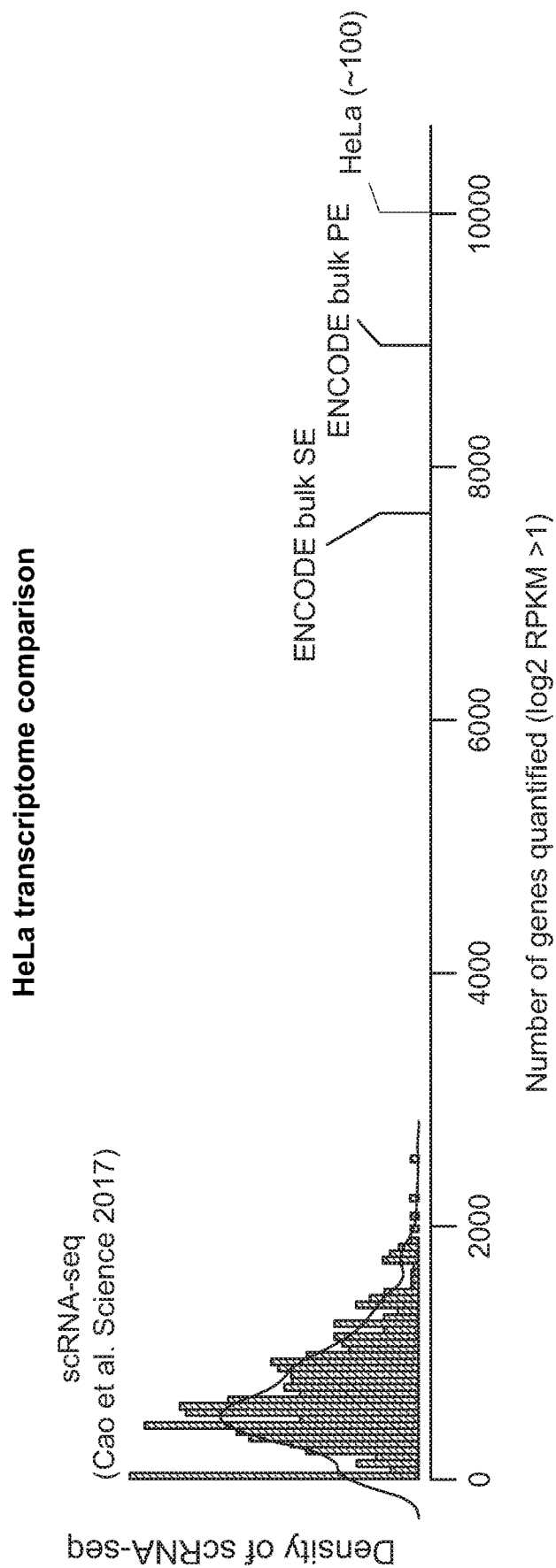
FIG. 3 is a graph illustrating data from a HeLa transcriptome comparison involving an embodiment of a method and/or process of the present disclosure. The x-axis corresponds to number of genes quantified (log 2 RPKM>1). The y-axis corresponds to density of scRNA-seq.
Figure 4:
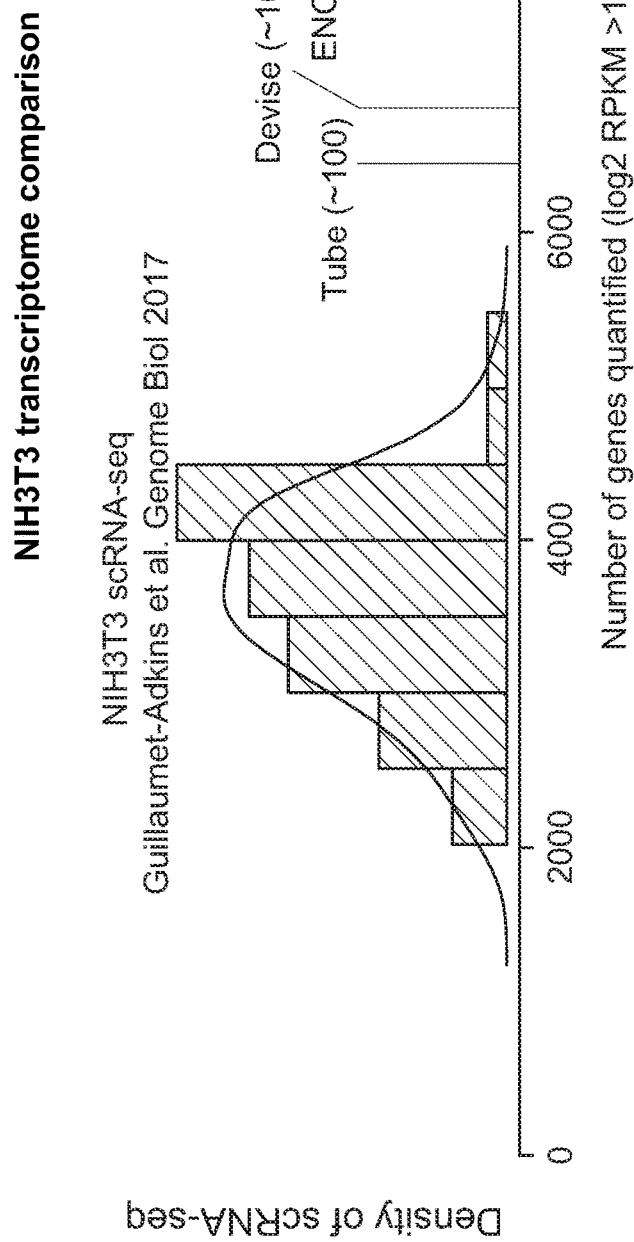
FIG. 4 is a graph illustrating data from an NH3T3 transcriptome comparison involving an embodiment of a method and/or process of the present disclosure. The x-axis corresponds to number of genes quantified (log 2 RPKM>1). The y-axis corresponds to density of scRNA-seq.

Based on preliminary finds, data indicated that we were surprisingly able to map more transcripts (10,000) onto the genome from the device data than the ENCODE dataset (7-9,000), and far more than the single cell dataset (<2000; see FIG. 3). This suggested that the device might be more sensitive than traditional approaches in detecting transcripts. We repeated the experiment with 3T3 cells, and included a 'tube' control (see FIG. 4). Here, we took ~100 cells in a tube, lysed them in the tube and amplified them. We also lysed ~100 cells on the device. We compared the sequence data against the ENCODE set and a published single cell 3T3 dataset. Both were better than single cell, but less than the ENCODE. However, what was interesting was that although the device transcriptome sequencing results had fewer reads than the tube sample, they mapped to more genes than the tube sample. This again is consistent with increased sensitivity on the device compared to traditional approaches.

The increased sensitivity was unexpected. It is contemplated that the reason for the increased sensitivity is because the device physically separates the RNA from the genomic DNA/chromatin with minimal manipulation.

This increase in sensitivity represents a novel advance over other current single cell approaches and even standard bulk RNA analysis. First, in regards to general transcriptome analysis, the standard approach for bulk RNA or single cell transcriptome studies is to use an oligodT primer to bind mRNA. However, analysis of single cell datasets clearly shows this approach can be highly inefficient. Low capture efficiency of mRNA in single cells has been known for several years to greatly limit the ability to detect the entire transcriptome of a cell. This means that many transcripts may never be detected using the standard oligodT primer, limiting the usefulness of the resulting transcriptome data. Furthermore, our results in FIG. 3 suggest this may also be the case for bulk RNA, as the ENCODE dataset detected fewer genes than using the device.

Furthermore, as new multi-omic approaches are being developed, oligodT has also been used to physically separate mRNA from genomic DNA. These "G and T" experiments use oligo-dT beads to purify the mRNA. However, this is likely to result in loss of the picogram quantities of material within the cell, because such steps involve washes and pipetting.

Figure 5:
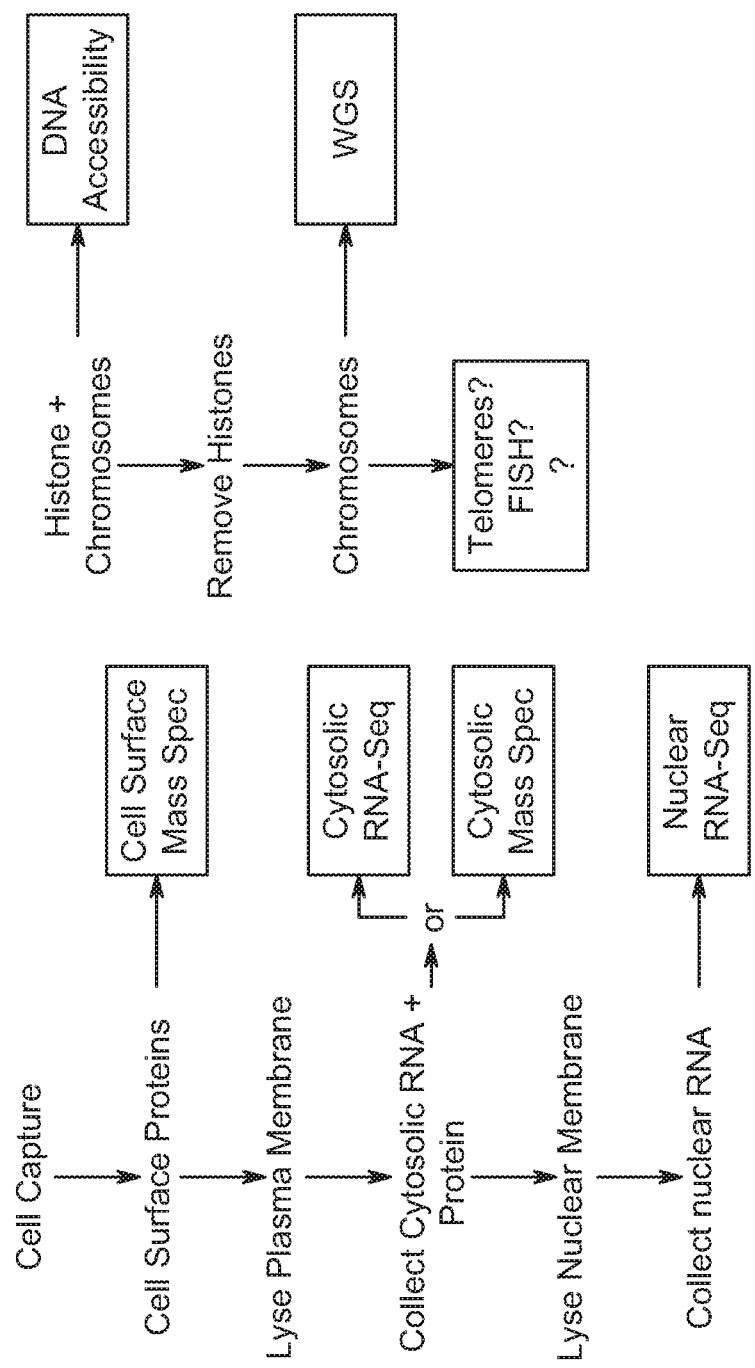
FIG. 5 is a schematic of various multi-omic workflows involving certain embodiments of the methods and/or processes of the present disclosure.

In contrast, by using the pillar-containing device we demonstrated our approach to separation results in very low loss of RNA. As evidenced in FIG. 4, the data suggested that we can detect at least as many, if not more, transcripts than bulk RNA from the ENCODE set. Further, as shown in FIG. 5, we can also identify more genes than a simple tube based approach because more reads can be mapped using the device. This increase in sensitivity was unexpected, and represents a major improvement over current state of the art.

A second concept is that we could further extend the separation of cellular analytes on the device. As shown in FIG. 5, it is possible to conceive of conditions where proteins on the surface are removed via some protease, and captured downstream. A lysis buffer that then lyses the extracellular membrane could then be flowed in, and allow cytosolic proteins and RNA to be captured. After adding a nuclear lysis buffer, chromatin could be analyzed. And after stripping chromatin, genomic DNA can then be analyzed. This would allow for several different –omic data to be obtained from the same cell.

We note that in addition to providing extended multi-omic analyses of single cells, that our method should also provide for highly increased sensitivity of detection for these other –omic approaches because of its simple separation design. Thus, we could potentially improve upon existing single cell proteomic analyses, or cytosolic analyses due to our increased sensitivity, regardless of whether these analyses are part of a multi-omic study. This extended multi-omic approach could therefore be of benefit by itself, any one –omic analysis could be enhanced due to increased sensitivity, or all the multi-omic data resulting from the device could be an improvement over standard approaches because of increased sensitivity.

It is contemplated that this is the basis for two separate new technologies: first, the separation increases the sensitivity of detection of separated analytes; and second, the device can be used to do multi-omic analysis of various analytes. The increase in sensitivity could aid in the analysis of any one isolated analyte (e.g. RNA only) or potentially the sensitivity of all analytes tested in a multi-omic analysis (e.g., genomic DNA and RNA).

Example 2

Analysis of Cell Analytes Using Micropillar Technology

Various experiments have been conducted to isolate and analyze various types of analyte components from cell samples using the micropillar technology of the present disclosure. Data from these experiments are illustrated in FIGS. 6-10, as further discussed below.

Figure 6:
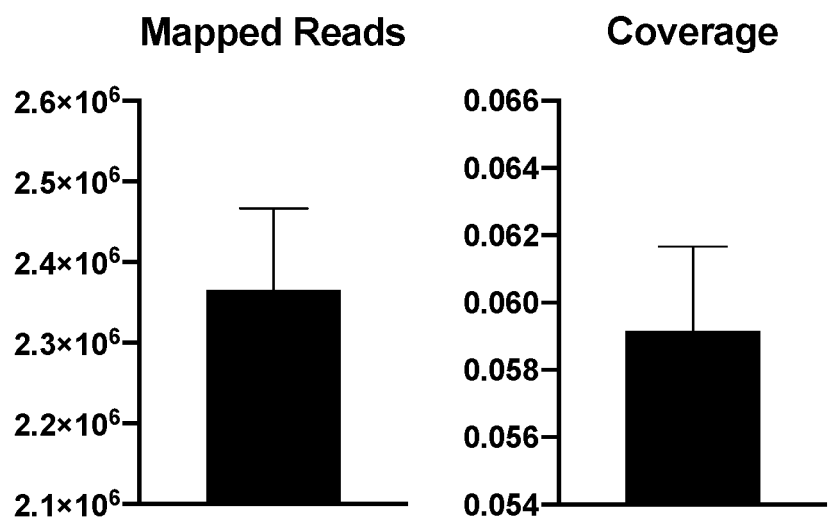
FIG. 6 is a graph illustrating data of a shallow depth whole genome sequencing of gDNA from single HeLa cells isolated via a micropillar array according to embodiments of the present disclosure.

FIG. 6 shows data of shallow depth whole genome sequencing of gDNA from single HeLa cells isolated via a micropillar array according to embodiments of the present disclosure. This data relates to the whole genome analyte (Class 5) and is whole genome sequencing data from single Hela cells, demonstrating that whole genome amplification on the microfluidic device of the present disclosure from single cells can be recovered and mapped to the human genome (n=3).

Figure 7:
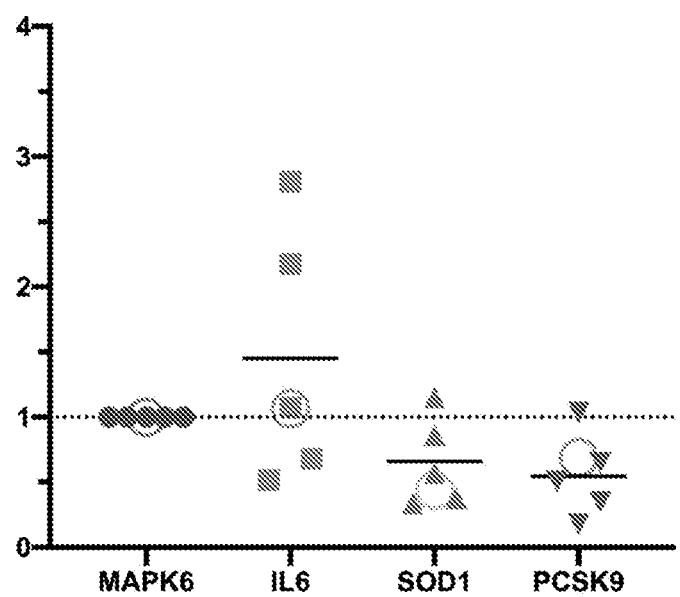
FIG. 7 is a graph illustrating data of an amplification uniformity of multi-cell gDNA isolated on micropillars using multiple displacement amplifications (MDAs) according to embodiments of the present disclosure.

FIG. 7 shows data of amplification uniformity of multi-cell gDNA isolated on micropillars using multiple displacement amplifications (MDAs) according to embodiments of the present disclosure. This data relates to the whole genome analyte (Class 5), and demonstrates the uniformity of whole genome amplification from multi-cell samples across 4 genetic loci using qPCR. The Y-axis is "relative amount" and the X-axis is 4 different genes tested. Every data point has been normalized to MAPK6 (Y=1, dotted line). There are two forms of data on the graph, the open-colored circles, and the corresponding filled in colored circles/squares/triangles. The open-circles represent the "reference" uniformity of each gene compared to MAPK6 in unamplified gDNA purified off the device. Thus, for example, when assayed with qPCR, SOD1 is roughly 0.5× as abundant as MAPK6, indicating that more copies of MAPK6 are present than SOD1 in the unamplified Hela genome. Each filled in point represents a replicate from gDNA amplification on the device (n=5). The main point is that the mean values (black bars) match very closely to the mean reference value, indicating that the amplification on the microfluidic device of the present disclosure did not introduce biased amplifications caused by differential amplifications across different regions.

Figure 8:
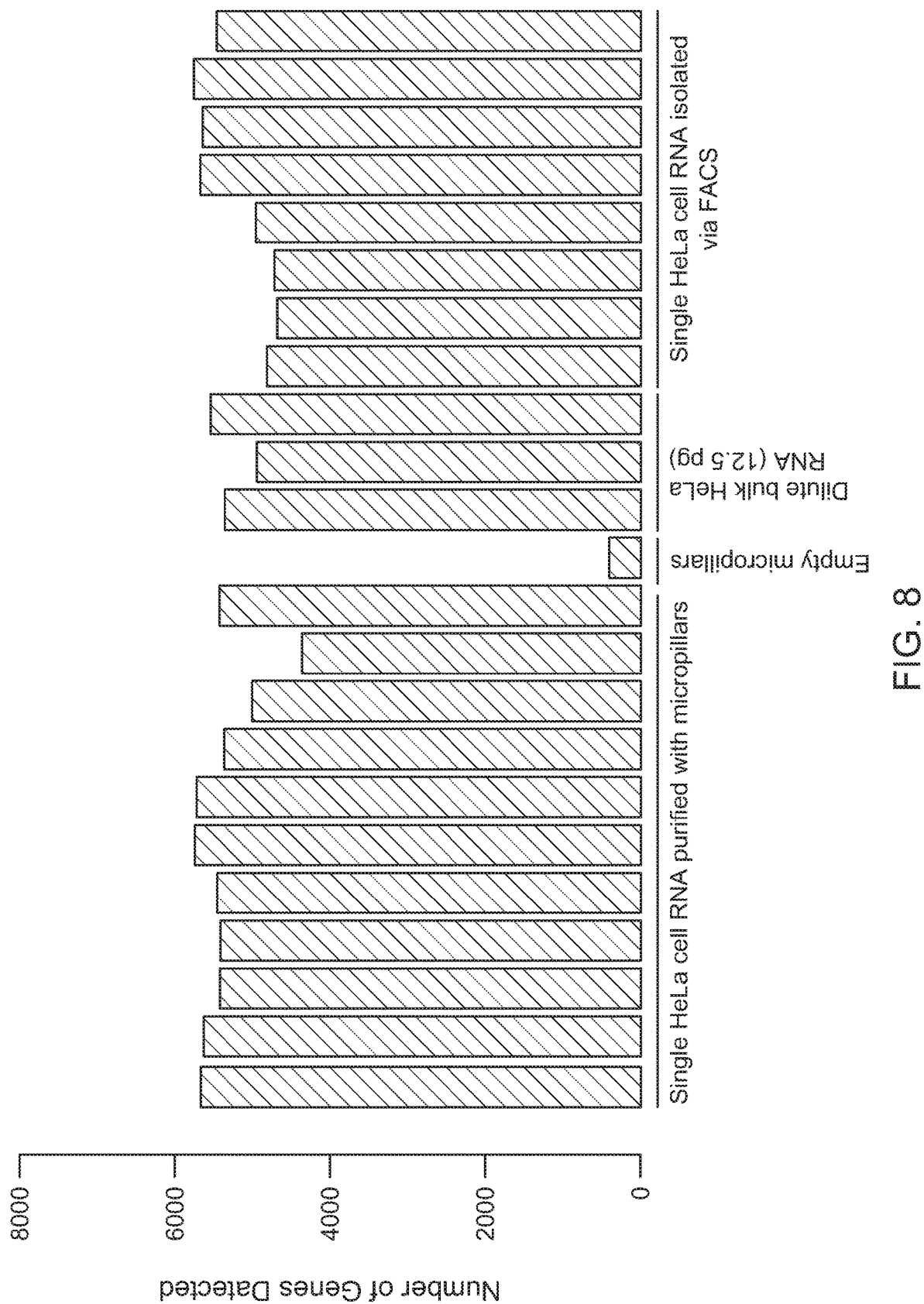
FIG. 8 is a graph illustrating data of a comparison of number of genes detected from single HeLa cell RNA purified with micropillar technology and single HeLa cell RNA isolated via FACS according to embodiments of the present disclosure.

FIG. 8 shows data of a comparison of number of genes detected from single HeLa cell RNA purified with micropillar technology and single HeLa cell RNA isolated via FACS according to embodiments of the present disclosure. This data relates to the total RNA analyte (Classes 2 and 3). These data are RNA-seq results showing the number of genes detected from single-cell total RNA purified from the device (n=11), an empty channel without any cells of the device (n=1), dilute bulk HeLa RNA mimicking a single cell (n=3), and single-cell total RNA from FACS isolated cells (n=8). The main points here are (1) RNA purified with the micropillars is demonstrated, (2) empty channels processed for RNA demonstrate low background, and (3) number of genes detected from single cells from RNA purified with the micropillars of the present disclosure is comparable to RNA from single cells isolated via FACS.

Figure 9C:
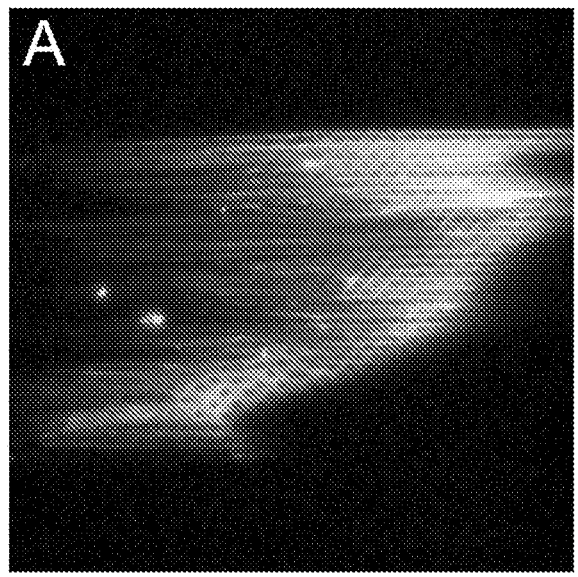
Figure 9C:
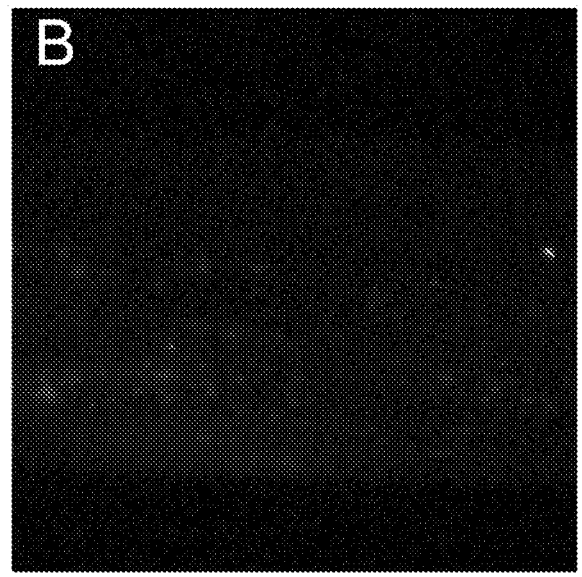
Figure 9C:
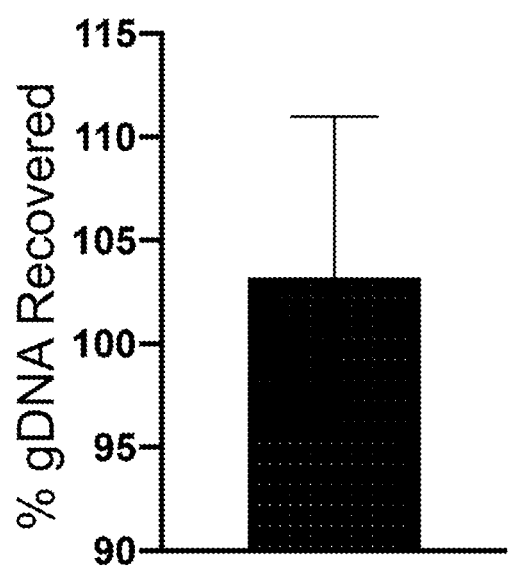

FIGS. 9A-9C show data illustrating that gDNA trapped on micropillars can be recovered using restriction enzymes with high efficiency according to embodiments of the present disclosure. This data supports analyte Class 6 (recovery of trapped gDNA from micropillars of the present disclosure for off-chip DNA analysis such as methylation analysis). FIG. 9A shows gDNA from lysed cells (multi-cell sample) that was trapped and visualized with PicoGreen. FIG. 9B shows that PicoGreen signal disappears post restriction enzyme treatment. FIG. 9C indicates that ~100% of expected gDNA that was trapped is recovered from the output port post digestion (calculated from # of cells that were trapped in array before lysis). Some values exceed 100% because expected yield is an estimate based on how much DNA there is per cell (n=2).

Figure 10A:
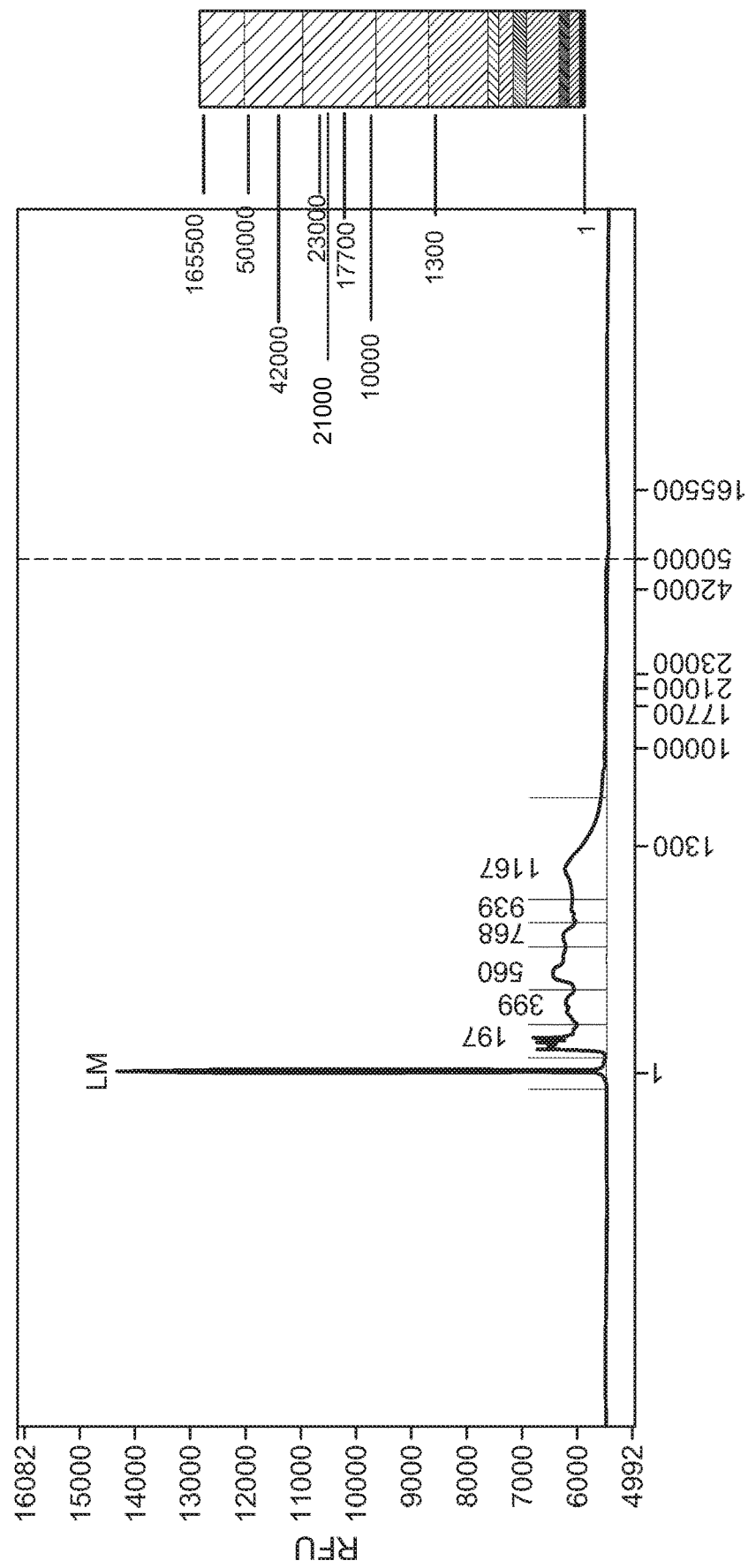
FIGS. 10A-10B are graphs illustrating data showing that recovery of gDNA trapped on micropillars via restriction enzyme digestion of gDNA trapped on micropillars yields large fragments of gDNA according to embodiments of the present disclosure.
Figure 10B:
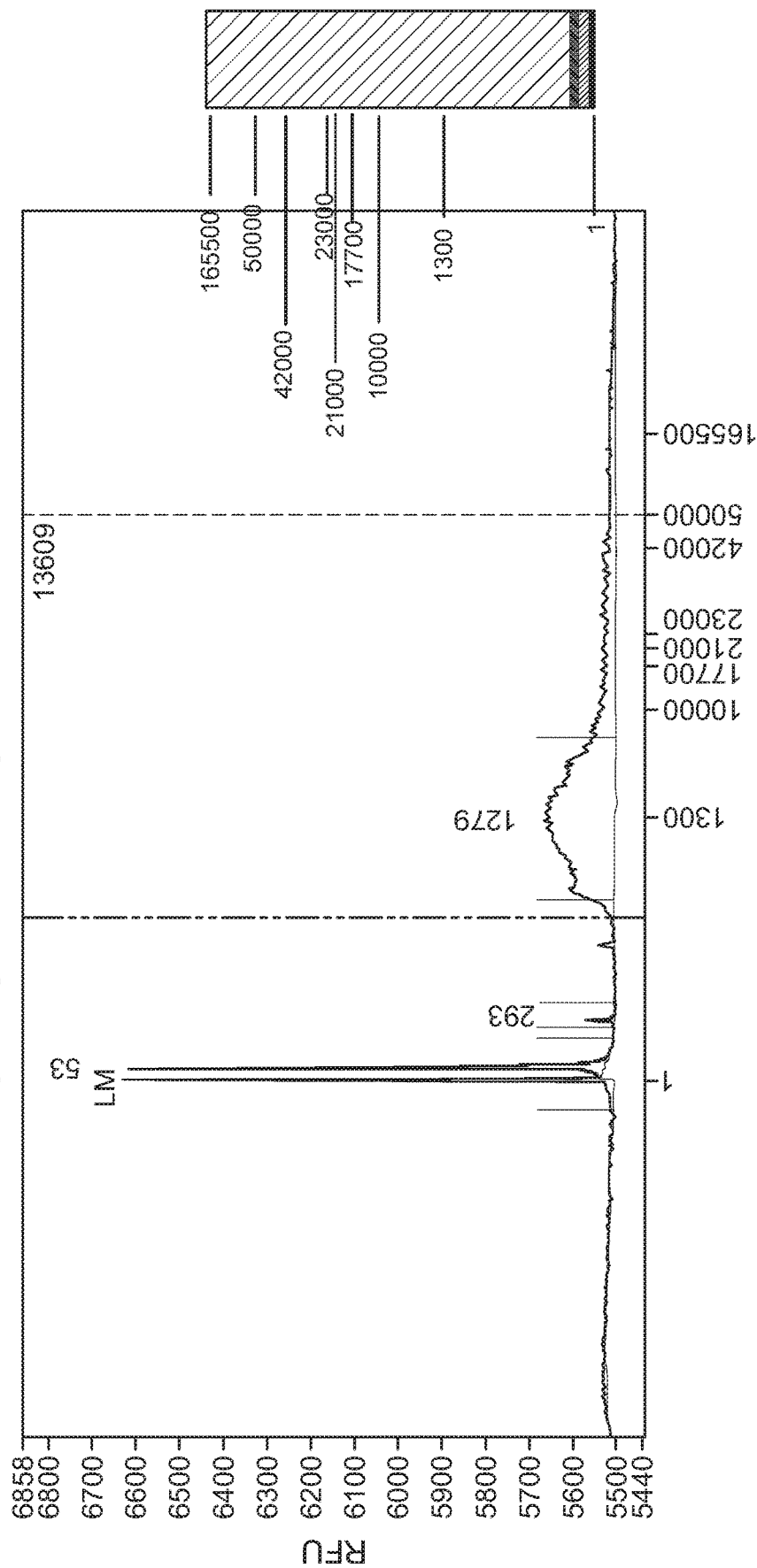

FIGS. 10A-10B show data illustrating that recovery of gDNA trapped on micropillars via restriction enzyme digestion of gDNA trapped on micropillars yields large fragments of gDNA according to embodiments of the present disclosure. This data is in support of analyte Class 6 (off-chip DNA analysis such as methylation analysis). FIG. 10A shows that HeLa gDNA purified through standard kits and digested with a restriction enzyme in a tube (standard methods) produces a range of small fragments (~190 bp to 2 kb) when run on a fragment analyzer. In contrast, as shown in FIG. 10B, gDNA from ~100 cells that was isolated on micropillars according to the present disclosure and recovered via restriction digest (same enzyme as used for generating the data in FIG. 10A) produces a broad spectrum of much large fragment sizes (~800 bp to 500 kb). Notably absent from this approach are small fragments present in the tube based digest. This means that gDNA recovered from the micropillars of the present disclosure is well suited for any further type of gDNA analysis off-chip. For example, this range of fragment sizes is more than ideal for bisulfite sequencing analysis, but could be used for any other analysis that requires large fragments of gDNA such as long-read DNA sequencing.

Illustrative embodiments of the processes, methods, and products of the present disclosure are described herein. It should be understood, however, that the description herein of the specific embodiments is not intended to limit the present disclosure to the particular forms disclosed but, on the contrary, the intention is to cover all modifications, equivalents, and alternatives falling within the spirit and scope of the invention by the appended claims. Thus, although the present invention has been described for the purpose of illustration, it is understood that such detail is solely for that purpose and variations can be made by those skilled in the art without departing from the spirit and scope of the invention which is defined by the following claims.

What is claimed is:

1. A method for isolating one or more distinct analyte component from a cell sample, said method comprising the acts of:
   introducing, under continuous flow conditions, a cell sample comprising at least one cell into a microfluidic device comprising an array of cell capture micropillars and a plurality of nucleic acid entanglement micropillars
   capturing the at least one cell in the array of cell capture micropillars while the microfluidic device is subjected to a continuous flow rate;
   treating the at least one captured cell with a sequential workflow procedure under conditions effective to separate at least one analyte therefrom, wherein said analyte is selected from the group consisting of: (i) a total protein fraction; (ii) a plasma membrane protein fraction; (iii) a total RNA fraction; (iv) a cytosolic RNA fraction; (v) a cytosolic protein fraction; (vi) a nuclear RNA fraction; (vii) a nuclear protein fraction; (viii) a chromatin fraction comprising genomic DNA (gDNA) regions of open chromatin; (ix) a gDNA markers fraction comprising epigenetic and regulatory markers of gDNA; (x) an amplified gDNA fraction; and (xi) a methylated gDNA fraction, wherein said gDNA is single-stranded gDNA, double-stranded gDNA, or a combination of single-and double-stranded gDNA; and
   isolating the analyte in a manner suitable for further testing and/or analysis thereof.

2. The method according to claim 1, wherein the sequential workflow procedure comprises implementing a separation protocol to separate a plurality of distinct classes of analyte component from the cell sample, and wherein the sequential workflow procedure requires that only one distinct analyte component can be isolated per class.

3. The method according to claim 2, wherein the separation protocol is for separating the total protein fraction from the cell sample and comprises flowing a total protein treatment solution through the microfluidic device under continuous flow conditions effective to release the total protein fraction from the one or more captured cell, thereby causing the total protein fraction to flow out of the microfluidic device.

4. The method according to claim 2, wherein the separation protocol is for separating the plasma membrane protein fraction from the cell sample and comprises flowing a plasma membrane protein treatment solution through the microfluidic device under continuous flow conditions effective to cleave proteins from plasma membranes of the one or more captured cell without lysing the plasma membranes, thereby causing the plasma membrane protein fraction to flow out of the microfluidic device.

5. The method according to claim 2, wherein the separation protocol is for separating the total RNA fraction from the cell sample and comprises flowing a total RNA treatment solution through the microfluidic device under continuous flow conditions effective to release the total RNA fraction from the one or more captured cell, thereby causing the total RNA fraction to flow out of the microfluidic device.

6. The method according to claim 2, wherein the separation protocol is for separating the cytosolic RNA fraction from the cell sample and comprises flowing a cytosolic RNA treatment solution through the microfluidic device under continuous flow conditions effective to release the cytosolic RNA fraction from the one or more captured cell, thereby causing the cytosolic RNA fraction to flow out of the microfluidic device.

7. The method according to claim 2, wherein the separation protocol is for separating the cytosolic protein fraction from the cell sample and comprises flowing a cytosolic protein treatment solution through the microfluidic device under continuous flow conditions effective to release the cytosolic protein fraction from the one or more captured cell, thereby causing the cytosolic protein fraction to flow out of the microfluidic device.

8. The method according to claim 2, wherein the separation protocol is for separating the nuclear RNA fraction from the cell sample and comprises flowing a nuclear RNA treatment solution through the microfluidic device under continuous flow conditions effective to release the nuclear RNA fraction from the one or more captured cell, thereby causing the nuclear RNA fraction to flow out of the microfluidic device.

9. The method according to claim 2, wherein the separation protocol is for separating the nuclear protein fraction from the cell sample and comprises flowing a nuclear protein treatment solution through the microfluidic device under continuous flow conditions effective to release the nuclear protein fraction from the one or more captured cell, thereby causing the nuclear protein fraction to flow out of the microfluidic device.

10. The method according to claim 2, wherein the separation protocol is for separating the chromatin fraction from the cell sample and comprises flowing a chromatin treatment solution through the microfluidic device under continuous flow conditions effective to release the chromatin fraction from the one or more captured cell, thereby causing the chromatin fraction to flow out of the microfluidic device.

11. The method according to claim 2, wherein the separation protocol is for separating the gDNA markers fraction from the cell sample and comprises flowing a gDNA markers treatment solution through the microfluidic device under continuous flow conditions effective to release the gDNA markers fraction from the one or more captured cell, thereby causing the gDNA markers fraction to flow out of the microfluidic device.

12. The method according to claim 2, wherein the separation protocol is for separating the amplified gDNA fraction from the cell sample and comprises flowing an amplified gDNA treatment solution through the microfluidic device under continuous flow conditions effective to release the amplified gDNA fraction from the one or more captured cell, thereby causing the amplified gDNA fraction to flow out of the microfluidic device.

13. The method according to claim 2, wherein the separation protocol is for separating the methylated gDNA fraction from the cell sample and comprises flowing a methylated gDNA treatment solution through the microfluidic device under continuous flow conditions effective to release the methylated gDNA fraction from the one or more captured cell, thereby causing the methylated gDNA fraction to flow out of the microfluidic device.

14. The method according to claim 2, wherein said act of treating comprises implementing a combination of the separation protocols to isolate one or more of the distinct analyte components for purposes of single or multiomic analysis thereof.

15. The method according to claim 1, wherein the cell sample is a single cell or multiple cells.

16. The method according to claim 1, wherein the cell sample is selected from the group consisting of a cancer cell, a primary cell type isolated from tissue of a human, an animal, or a plant, and an immortalized cell line.

17. The method according to claim 1, wherein the flow rate ranges from between 0.001 nL/minute and 100 uL/minute.

18. The method according to claim 1, further comprising analyzing the at least one analyte.

19. The method according to claim 18, wherein the at least one analyte is a plasma membrane protein fraction, a total protein fraction, a cytosolic protein fraction, and/or a nuclear protein fraction that is subjected to further testing and/or analysis selected from the group consisting of mass spectrometry, immuno-based detection assays, and aptamer-based detection assays.

20. The method according to claim 18, wherein the at least one analyte is a total RNA fraction, a cytosolic RNA fraction, a nuclear RNA fraction, and/or a chromatin fraction that is subjected to further testing and/or analysis selected from the group consisting of transcriptome analysis via RNA-seq, targeted gene expression profiling via RT-PCR, or RT-qPCR.

21. The method according to claim 18, wherein the one or more distinct analyte component is a gDNA markers fraction and/or an amplified gDNA fraction that is subjected to further testing and/or analysis selected from the group consisting of whole genome sequencing, exome sequencing, targeted re-sequencing, PCR, and qPCR.

22. The method according to claim 18, wherein the one or more distinct analyte component is a methylated gDNA fraction that is subjected to further testing and/or analysis selected from the group consisting of bisulfite conversion analysis, methylation specific PCR, methylation specific qPCR, reduced representation bisulfite sequencing, and whole genome bisulfite sequencing.

23. The method according to claim 1, wherein the sequential workflow procedure comprises implementing a separation protocol to separate a plurality of distinct classes of analyte component from the cell sample, wherein the distinct classes comprise:
- Class 1: the total protein and plasma membrane protein fractions;
- Class 2: the total protein, total RNA, cytosolic RNA, and cytosolic protein fractions;
- Class 3: the total protein, total RNA, nuclear RNA, and nuclear protein fractions;
- Class 4: the chromatin fraction;
- Class 5: the gDNA markers and amplified gDNA fractions; and
- Class 6: the gDNA markers and methylated gDNA fractions, wherein the sequential workflow procedure operates under the following rules:
- Rule A: only one distinct analyte component can be isolated per class;
- Rule B: isolation of one or more of the classes may start with any of the classes;
- Rule C: if more than one class is to be isolated, the order of isolation must proceed progressively along a classification gradient that includes, in sequence, Class 1, Class 2, Class 3, Class 4, Class 5, and Class 6, where Class 1 represents the start of the classification gradient and Class 6 represents the end of the classification gradient;
- Rule D: if more than one class is to be isolated, the classes to be isolated will begin with an initial class comprising the class closest to the start of the classification gradient and terminate with a terminal class comprising the class closest to the end of the classification gradient; and
- Rule E: if more than one class is to be isolated, any intermediate class falling between the initial class and the terminal class of the classification gradient may either be omitted or included from the isolating process.

* * * * *